(12) United States Patent
Shibasaki et al.

(10) Patent No.: US 8,785,690 B2
(45) Date of Patent: Jul. 22, 2014

(54) THIOAMIDE COMPOUND, METHOD FOR PRODUCING THIOAMIDE COMPOUND, METHOD FOR PRODUCING [(4R,6R)-6-AMINOETHYL-1,3-DIOXAN-4-YL]ACETATE DERIVATIVE, AND METHOD FOR PRODUCING ATORVASTATIN

(71) Applicant: Microbial Chemistry Research Foundation, Tokyo (JP)

(72) Inventors: Masakatsu Shibasaki, Tokyo (JP); Naoya Kumagai, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 13/971,186

(22) Filed: Aug. 20, 2013

(65) Prior Publication Data
US 2013/0338375 A1 Dec. 19, 2013

Related U.S. Application Data

(63) Continuation of application No. PCT/JP2012/053323, filed on Feb. 14, 2012.

(30) Foreign Application Priority Data

Feb. 21, 2011 (JP) .................. 2011-035006

(51) Int. Cl.
*C07C 327/42* (2006.01)
*C07D 207/34* (2006.01)

(52) U.S. Cl.
CPC ............ *C07C 327/42* (2013.01); *C07D 207/34* (2013.01)
USPC ............................................. 564/74; 548/461

(58) Field of Classification Search
CPC ........................... C07C 327/42; C07D 207/34
USPC ........................................... 564/74; 548/461
See application file for complete search history.

(56) References Cited

U.S. PATENT DOCUMENTS 5,273,995 A 12/1993 Roth

FOREIGN PATENT DOCUMENTS

WO 2004/015132 2/2004

OTHER PUBLICATIONS

Roth, B.D., "The Discovery and Development of Atorvastatin, a Potent Novel Hypolipidemic Agent," Progress in Medicinal Chemistry, vol. 40, 2002, pp. 1-22.
Brower, P.L., "The Synthesis of (4R-cis)-1,1-Dimethylethyl 6-cyanomethyl-2,2-dimethyl-1,3-dioxane-4-acetate, a Key Intermediate for the Preparation of CI-981, a Highly Potent, Tissue Selective Inhibitor of HMG-CoA Reductase," Tetrahedron Letters, vol. 33, No. 17, 1992, pp. 2279-2282.
Rádl, S., "A New Way to *tert*-Butyl [(4R,6R)-6-Aminoethyl-2,2-dimethyl-1,3-dioxan-4-yl]acetate, a Key Intermediate of Atorvastatin Synthesis," Synthetic Communications, vol. 33, No. 13, 2003, pp. 2275-2283.
Iwata, M., et al., "Direct Catalytic Asymmetric Aldol Reactions of Thioamides: Toward a Stereocontrolled Synthesis of 1,3-Polyols," Journal of the American Chemistry Society, vol. 131, No. 51, 2009, pp. 18244-18245.
Iwata, M., et al., "Catalytic Asymmetric Direct Aldol Reaction of Thioamide," Proceedings 2 of the 130th Annual Meeting of the Pharmaceutical Society of Japan, Mar. 5, 2010, p. 122, Lecture No. 30TF-am07.
Kawato, Y., et al., "A Simplified Catalytic System for Direct Catalytic Asymmetric Aldol Reaction of Thioamides: Application to an Enantioselective Synthesis of Atorvastatin," Tetrahedron, vol. 67, 2011, pp. 6539-6546, available online Jun. 2, 2011.
Kawato, Y., et al., "Study on Efficient Asymmetric Synthesis of Atorvastatin Utilizing Catalytic Asymmetric Direct Aldol Reaction of Thioamide," Proceedings 2 of the 131st Annual Meeting of the Pharmaceutical Society of Japan, Mar. 5, 2011, p. 172, Lecture No. 31P-0202.

*Primary Examiner* — Robert Havlin
(74) *Attorney, Agent, or Firm* — Carmody Torrance Sandak & Hennessey LLP

(57) ABSTRACT

A thioamide compound represented by the following general formula (1):

General Formula (1)

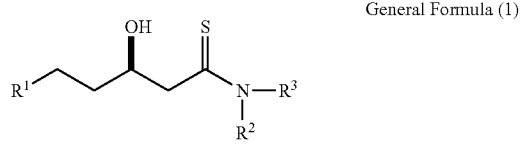

wherein, in the general formula (1), $R^1$ represents one of $-OR^{11}$ and $-NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure.

5 Claims, 2 Drawing Sheets

Atorvastatin calcium

[KRED = Ketoreductase
GDH = Glucose dehydrogenase
HHDH = Halohydrin dehalogenase]

THIOAMIDE COMPOUND, METHOD FOR PRODUCING THIOAMIDE COMPOUND, METHOD FOR PRODUCING [(4R,6R)-6-AMINOETHYL-1,3-DIOXAN-4-YL]ACETATE DERIVATIVE, AND METHOD FOR PRODUCING ATORVASTATIN

CROSS-REFERENCE TO RELATED APPLICATION

This application is a continuation application of International Application PCT/JP2012/053323 filed on Feb. 14, 2012 and designated the U.S., the entire contents of which are incorporated herein by reference.

BACKGROUND OF THE INVENTION

1. Field of the Invention

The present invention relates to a thioamide compound useful for the synthesis of atorvastatin, a method for producing the thioamide compound, a method for producing a [(4R,6R)-6-aminoethyl-1,3-dioxan-4-yl]acetate derivative using the thioamide compound, and a method for producing atorvastatin using the thioamide compound.

2. Description of the Related Art

Conversion of 3-hydroxy-3-methylglutaryl-coenzyme A (HMG-CoA) into mevalonate is a rate-determining step in the initial stage of the cholesterol biosynthetic pathway. This step is catalyzed by the enzyme HMG-CoA reductase. Statins inhibit the catalytic action of HMG-CoA reductase on this conversion. In light of this, on the whole, statins are potent lipid lowering substances.

Currently, atorvastatin calcium hydrate is commercially available as Lipitor (R), which has the following formula (see, for example, U.S. Pat. No. 5,273,995).

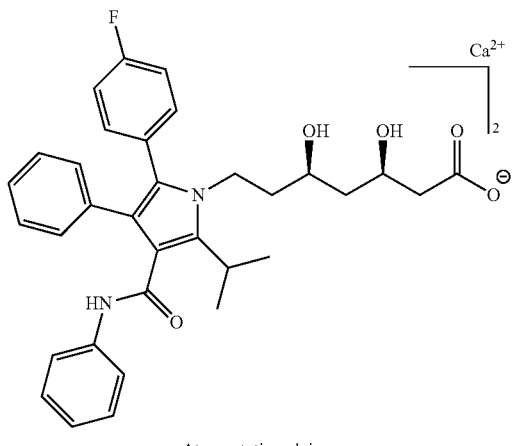

Atorvastatin calcium

Atorvastatin calcium is a selective, competitive HMG-CoA inhibitor. In light of this, atorvastatin is a potent lipid lowering substance, and therefore, is useful as a lipid lowering agent and/or cholesterol lowering agent. Further, atorvastatin is also useful for the treatment of osteoporosis, benign prostatic hyperplasia (BPH), and Alzheimer's disease.

As a method for synthesizing atorvastatin calcium, a synthesis method shown in FIG. 1 is known (see, for example, Roth B. D., et al., Progress in Medicinal Chemistry, 2002, 40, pp. 1 to 22).

However, a problem of the synthesis method shown in FIG. 1 is that this method is not suitable for industrial production since it uses HBr and NaCN and requires an ultra-low temperature step.

In light of the above, various studies have been conducted to search for a novel method for synthesizing atorvastatin.

For example, a method for synthesizing (4R-cis)-1,1-dimethylethyl 6-cyanoethyl-2,2-dimethyl-1,3-dioxane-4-acetate, which is a synthetic intermediate in the method for synthesizing atorvastatin shown in FIG. 1, has been proposed (see, for example, Philip L. Brower, et al., Tetrahedron Letters, Vol. 33, No. 17, pp. 2279 to 2282, 1992).

However, a problem of the technique proposed above is that although (4R-cis)-1,1-dimethylethyl 6-cyanoethyl-2,2-dimethyl-1,3-dioxane-4-acetate is synthesized via a benzenesulfonyl derivative, the benzenesulfonyl derivative does not have sufficient reactivity toward the subsequent step.

Also, a method for synthesizing the (4R-cis)-1,1-dimethylethyl 6-cyanoethyl-2,2-dimethyl-1,3-dioxane-4-acetate by an enzyme method has been proposed (see, for example, International Publication No. WO2004/015132).

The technique proposed above involves a reaction pathway shown in FIG. 2. A problem of this technique is that it requires complicated 3-step enzymatic reactions using three kinds of enzymes, which are ketoreductase (KRED), glucose dehydrogenase (GDH), and halohydrin dehalogenase (HHDH).

Also, as another method, a method for synthesizing tert-butyl [(4R,6R)-6-aminoethyl-2,2-dimethyl-1,3-dioxan-4-yl]acetate, which is an intermediate in the method for synthesizing atorvastatin shown in FIG. 1, has been proposed (see, for example, Stanislav Radl, SYNTHETIC COMMUNICATIONS, Vol. 33, No. 13, pp. 2275 to 2283, 2003).

However, a problem of the technique proposed above is that it requires complicated steps that require oxidation of primary alcohol for introduction of a nitrogen functional group, a nitroaldol reaction, and an elimination reaction for the resulting secondary alcohol.

Accordingly, the current situation is that there is a demand for the provision of a compound enabling the efficient production of a [(4R,6R)-6-aminoethyl-1,3-dioxan-4-yl]acetate derivative using a catalyst that can be prepared at low cost such as a copper catalyst, a method for producing the compound, a method for producing a [(4R,6R)-6-aminoethyl-1,3-dioxan-4-yl]acetate derivative using the compound, and a method for producing atorvastatin using the compound.

SUMMARY OF THE INVENTION

An object of the present invention is to solve the aforementioned various problems associated with the conventional art to achieve the following goal. That is, objects of the present invention are to provide a thioamide compound enabling the efficient production of a [(4R,6R)-6-aminoethyl-1,3-dioxan-4-yl]acetate derivative using a catalyst that can be prepared at low cost such as a copper catalyst, a method for producing the thioamide compound, a method for producing a [(4R,6R)-6-aminoethyl-1,3-dioxan-4-yl]acetate derivative using the thioamide compound, and a method for producing atorvastatin using the thioamide compound.

A means for achieving the above objects is as follows. That is,

<1> A thioamide compound represented by the following general formula (1):

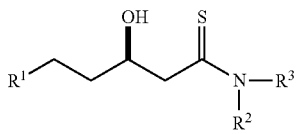

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure.

<2> A method for producing the thioamide compound according to <1>, the method including:

reacting a compound represented by the following general formula (2) with a compound represented by the following general formula (3):

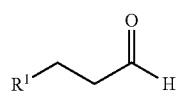

General Formula (2)

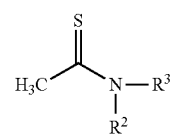

General Formula (3)

wherein, in the general formula (2), $R^1$ represents one of —$OR^{11}$ and —$NR^{12}R^{13}$; the represents one of a protecting group of a hydroxyl group and a hydrogen atom; the $R^{12}$ and $R^{13}$ each independently represent one of a hydrogen atom and a protecting group of an amino group, where the $R^{12}$ and $R^{13}$ may together form a protecting group having a cyclic structure; and in the general formula (3), $R^2$ and $R^3$ each independently represent one of a protecting group of an amide group and a hydrogen atom.

<3> The method for producing the thioamide compound according to <2>, wherein the reacting carried out with a copper complex.

<4> The method for producing the thioamide compound according to <3>, wherein the copper complex is a copper-optically active phosphine complex.

<5> A method for producing a [(4R,6R)-6-aminoethyl-1,3-dioxan-4-yl]acetate derivative, the method including:

converting a thioamide compound represented by the following general formula (1) into an acetate derivative represented by the following general formula (4):

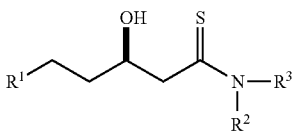

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure, and

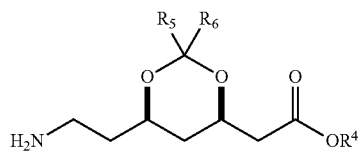

General Formula (4)

wherein, in the general formula (4), $R^4$ represents one of a protecting group of a carboxyl group and a hydrogen atom; and $R^5$ and $R^6$ each independently represent one of a hydrocarbon group having 1 to 6 carbon atoms and a hydrogen atom, where the $R^5$ and $R^6$ may together form a cyclic structure.

<6> A method for producing atorvastatin, including:

converting a thioamide compound represented by the following general formula (1) into an acetate derivative represented by the following general formula (4):

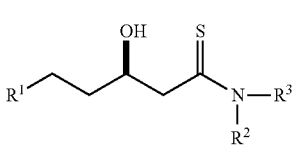

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure, and

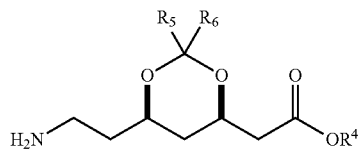

General Formula (4)

wherein, in the general formula (4), $R^4$ represents one of a protecting group of a carboxyl group and a hydrogen atom;

and $R^5$ and $R^6$ each independently represent one of a hydrocarbon group having 1 to 6 carbon atoms and a hydrogen atom, where the $R^5$ and $R^6$ may together form a cyclic structure.

The present invention can solve the aforementioned various problems associated with the conventional art to achieve the aforementioned goal, and moreover, provide a thioamide compound enabling the efficient production of a [(4R,6R)-6-aminoethyl-1,3-dioxan-4-yl]acetate derivative using a catalyst that can be prepared at low cost such as a copper catalyst, a method for producing the thioamide compound, a method for producing a [(4R,6R)-6-aminoethyl-1,3-dioxan-4-yl]acetate derivative using the thioamide compound, and a method for producing atorvastatin using the thioamide compound.

DETAILED DESCRIPTION OF THE INVENTION

Figure 1:
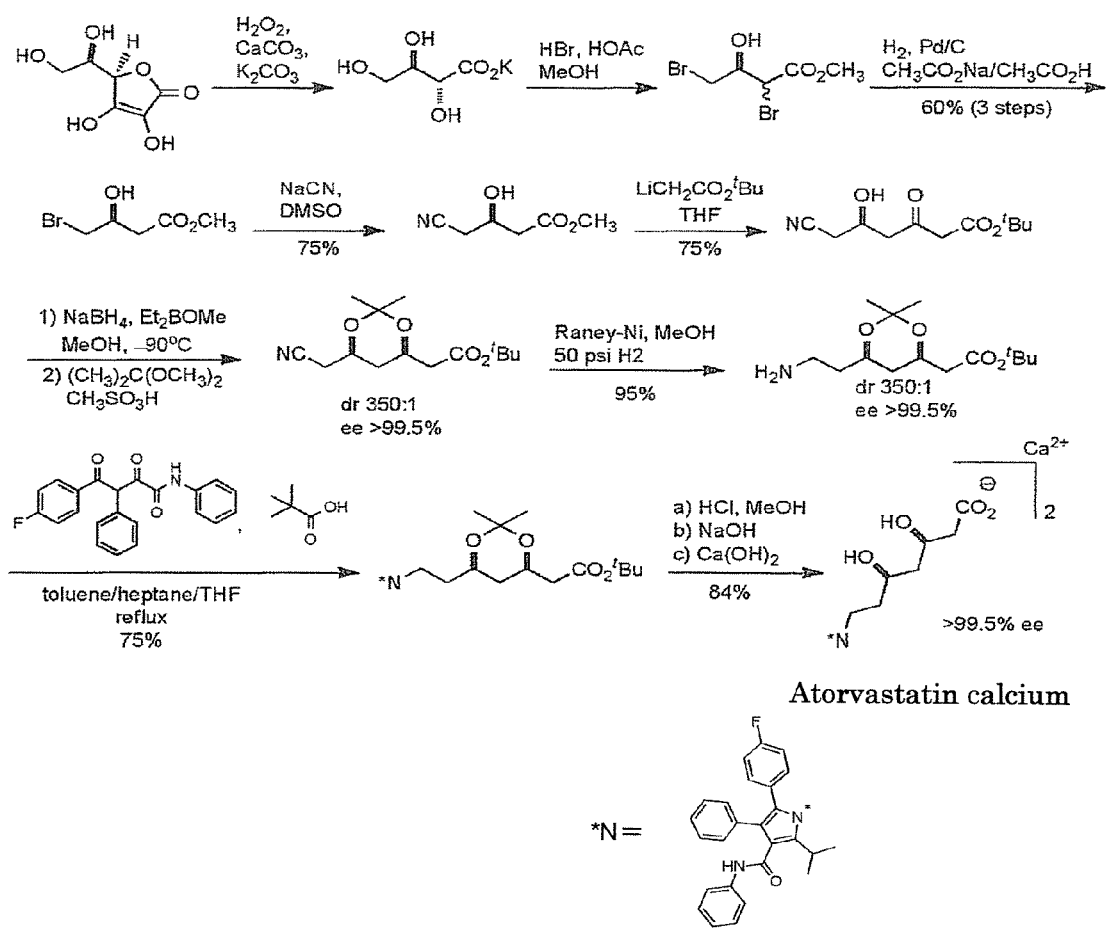
FIG. 1 is a synthesis scheme showing one example of the conventional method for synthesizing atorvastatin.
Figure 2:
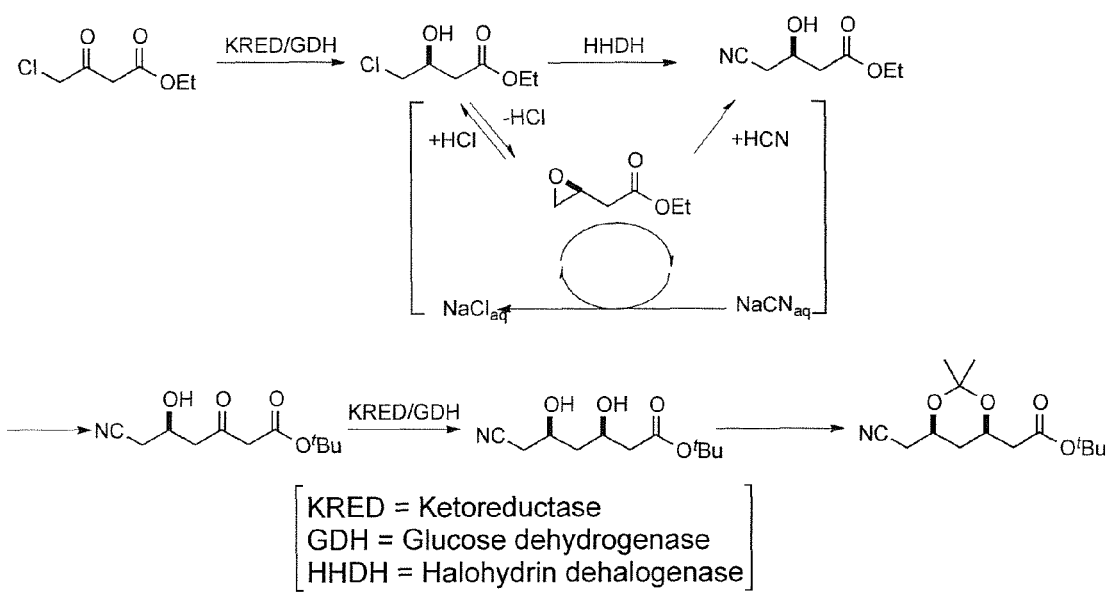
FIG. 2 is a synthesis scheme showing a method for synthesizing (4R-cis)-1,1-dimethylethyl 6-cyanoethyl-2,2-dimethyl-1,3-dioxane-4-acetate by an enzyme method.

Unless otherwise specifically noted, the configuration in the chemical formulae and general formulae shown in the present specification and claims represent the absolute configuration.
(Thioamide Compound)
The thioamide compound of the present invention is represented by the following general formula (1):

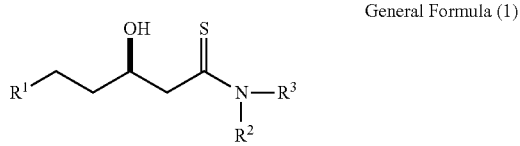

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure.

The protecting group of a hydroxyl group represented by the $R^{11}$ is not particularly limited and can be appropriately selected according to the purpose, and for example, books such as Green et al, Protective Groups in Organic Synthesis, 3rd Edition, 1999, John Wiley & Sons, Inc. can be referred to.

Examples of the protecting group of a hydroxyl group include an aralkyl group, a trialkylsilyl group, an alkoxyalkyl group, an alkanoyl group, and an arylcarbonyl group. When the aryl ring (such as a benzene ring) in the protecting group has a substituent, examples of the substituent include a halogen atom and an alkoxy group.

Examples of the aralkyl group include a benzyl group, a p-methoxybenzyl group, and a p-aminobenzyl group.

Examples of the trialkylsilyl group include a trimethylsilyl group, a triethylsilyl group, and a tert-butyldimethylsilyl group.

Examples of the alkoxyalkyl group include a methoxymethyl group and an ethoxymethyl group.

Examples of the alkanoyl group include an acetyl group and a trifluoroacetyl group.

Examples of the arylcarbonyl group include a benzoyl group and a substituted phenyl carbonyl group.

Among them, in terms of ease of deprotection in the synthesis of a [(4R,6R)-6-aminoethyl-1,3-dioxan-4-yl]acetate derivative, an aralkyl group is preferable, and a benzyl group is more preferable.

The protecting group of an amino group represented by the $R^{12}$ and $R^{13}$ is not particularly limited and can be appropriately selected according to the purpose. Examples thereof include a methoxycarbonyl group, a t-butoxycarbonyl group, a benzyloxycarbonyl group, an allyloxycarbonyl group, a formyl group, an acetyl group, a benzoyl group, a methyl group, an ethyl group, an allyl group, and a benzenesulfonyl group. Also, when the $R^{12}$ and $R^{13}$ together form a protecting group having a cyclic structure, examples of the protecting group include a phthaloyl group (Phth group). Among them, a phthaloyl group is preferable since it can be removed under mild reaction conditions.

The protecting group of an amide group represented by the $R^2$ and $R^3$ is not particularly limited and can be appropriately selected according to the purpose. Examples thereof include a tosyl group, a methoxymethyl group, a benzyloxymethyl group, an allyl group, a triisopropylsilyl group, a benzyl group, and a methoxycarbonyl group.

Among them, an allyl group is preferable since it yields excellent reaction results in the aldol reaction.

The thioamide compound of the present invention may also be obtained as a mixture of stereoisomers. In this case, such a mixture also falls within the scope of the present invention.

The method for producing a thioamide compound represented by the general formula (1) is not particularly limited and can be appropriately selected according to the purpose. However, the method for producing a thioamide compound according to the present invention that will be shown below is preferable.

The thioamide compound of the present invention is useful as a substance for the synthesis of a [(4R,6R)-6-aminoethyl-1,3-dioxan-4-yl]acetate derivative, which is a useful intermediate for the synthesis of atorvastatin, and further, as a substance for the synthesis of atorvastatin.
(Method for Producing a Thioamide Compound)
The method for producing a thioamide compound according to the present invention is a method for producing the thioamide compound of the present invention represented by the general formula (1), and it includes the step of reacting a compound represented by the following general formula (2) with a compound represented by the following general formula (3), and if necessary, further includes other steps:

General Formula (2)

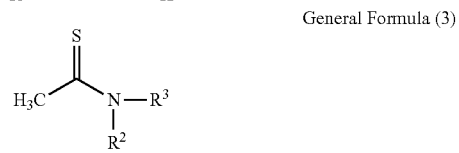

General Formula (3)

wherein, in the general formula (2), $R^1$ represents one of —$OR^{11}$ and —$NR^{12}R^{13}$; the $R^{11}$ represents one of a protecting group of a hydroxyl group and a hydrogen atom; the $R^{12}$ and $R^{13}$ each independently represent one of a hydrogen atom and a protecting group of an amino group, where the $R^{12}$ and $R^{13}$ may together form a protecting group having a cyclic structure; and in the general formula (3), $R^2$ and $R^3$ each independently represent one of a protecting group of an amide group and a hydrogen atom.

$R^1$ in the general formula (2) is the same as $R^1$ in the general formula (1).

$R^2$ and $R^3$ in the general formula (3) are the same as $R^2$ and $R^3$ in the general formula (1), respectively.

<Reaction Step>

The reaction step is not particularly limited as long as it is a step of reacting a compound represented by the general formula (2) with a compound represented by the general formula (3), and can be appropriately selected according to the purpose. It is preferable to use a copper complex. By using the copper complex as a catalyst in the reaction step, a thioamide compound represented by the general formula (1) can be produced using inexpensive copper as a catalyst source.

The copper complex is not particularly limited and can be appropriately selected according to the purpose; however, it is preferably a copper-optically active phosphine complex since excellent enantioselectivity is achieved.

The copper-optically active phosphine complex is a complex of copper and an optically active phosphine ligand. The optically active phosphine ligand is not particularly limited and can be appropriately selected according to the purpose. Examples thereof include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis-(diphenylphosphino)pentane (SKEWPHOS), 1,2-bis(substituted phospholano)benzene (DuPHOS), 1,2-bis(substituted phospholano)ethane (BPE), 1-(substituted phospholano)-2-(diphenylphosphino)benzene (UCAP-Ph), 1-(bis(3,5-dimethylphenyl)phosphino)-2-(substituted phospholano)benzene (UCAP-DM), 1-(substituted phospholano)-2-(bis(3,5-di(t-butyl)-4-methoxyphenyl)phosphino)benzene (UCAP-DTBM), 1-(substituted phospholano)-2-(di-naphthalen-1-yl-phosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8',-octahydrobinaphthyl) ($H_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6), (5',6')-bis(methylenedioxy)biphenyl-2,2'-diyl) (bisdiphenylphosphine) (SEGPHOS), ((5,6), (5',6')-bis(methylenedioxy)biphenyl-2,2'-diyl) (bis(3,5-dimethylphenyl)phosphine) (DM-SEGPHOS), and ((5,6), (5',6')-bis(methylenedioxy)biphenyl-2,2'-diyl) (bis(3,5 di (tert-butyl)-4-methoxyphenyl)phosphine) (DTBM-SEGPHOS).

Among them, (S,S)-2,5-substituted-BPE is preferable, and (S,S)-Ph-BPE is more preferable since excellent enantioselectivity is achieved.

It is to be noted that (S,S)-Ph-BPE is a compound represented by the following structural formula:

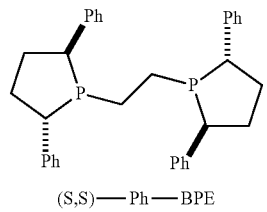

wherein, "Ph" represents a phenyl group.

Also, in the aldol reaction between thioamide and aldehyde, when there is an acidic hydrogen atom at the α-position of aldehyde, a large quantity of catalyst is required since thioamide is activated stoichiometrically when ordinary catalysts are used.

However, even when there is an acidic hydrogen atom at the α-position of aldehyde in an aldol reaction using thioamide (a compound represented by the general formula (3)), the thioamide compound represented by the general formula (1) can be produced through catalytic (i.e., not stoichiometric) activation of thioamide by using the copper-optically active phosphine complex.

Therefore, the copper-optically active phosphine complex may be used in a catalytic amount. The catalytic amount is preferably 1 mol % to 9 mol % relative to the compound represented by the general formula (2).

The ratio between the compound represented by the general formula (2) and the compound represented by the general formula (3) in the above reaction step is not particularly limited and can be appropriately selected according to the purpose. However, the ratio of the compound represented by the general formula (3) to the compound represented by the general formula (2) is preferably 1.0 equivalent to 1.5 equivalents.

A solvent to be used in the above reaction step is not particularly limited and can be appropriately selected according to the purpose. Examples thereof include tetrahydrofuran (THF) and N,N-dimethylformamide (DMF).

The reaction temperature in the above reaction step is not particularly limited and can be appropriately selected according to the purpose, and it is preferably −60° C. to −40° C.

The reaction time in the above reaction step is not particularly limited and can be appropriately selected according to the purpose, and it is preferably five hours to 36 hours.

The thioamide compound obtained by the method for producing a thioamide compound according to the present invention may also be obtained as a mixture of stereoisomers. In this case, such a mixture also falls within the scope of the present invention.

The thioamide compound represented by the general formula (1) obtained by the production method of the present invention is useful as a substance for the synthesis of a [(4R,6R)-6-aminoethyl-1,3-dioxan-4-yl]acetate derivative, which is a useful intermediate for the synthesis of atorvastatin, and further, as a substance for the synthesis of atorvastatin.

(Method for Producing a [(4R,6R)-6-aminoethyl-1,3-dioxan-4-yl]acetate Derivative)

The method for producing a [(4R,6R)-6-aminoethyl-1,3-dioxan-4-yl]acetate derivative according to the present invention includes the step of converting a thioamide compound represented by the general formula (1) into an acetate derivative represented by the following general formula (4), and if necessary, further includes other steps.

<Step of Conversion>

The step of conversion is not particularly limited as long as it is a step of converting a thioamide compound represented by the general formula (1) into an acetate derivative represented by the following general formula (4), and can be appropriately selected according to the purpose:

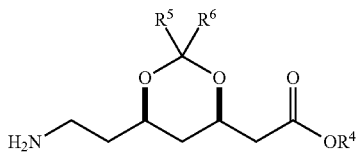

General Formula (4)

wherein, in the general formula (4), $R^4$ represents one of a protecting group of a carboxyl group and a hydrogen atom; and $R^5$ and $R^6$ each independently represent one of a hydrocarbon group having 1 to 6 carbon atoms and a hydrogen atom, where the $R^5$ and $R^6$ may together form a cyclic structure.

The protecting group of a carboxyl group represented by the $R^4$ is not particularly limited and can be appropriately selected according to the purpose, and for example, books such as Green et al, Protective Groups in Organic Synthesis, 3rd Edition, 1999, John Wiley & Sons, Inc. can be referred to.

Examples of the protecting group of a carboxyl group include an alkyl group and a trialkylsilyl group.

Examples of the alkyl group include a methyl group, an ethyl group, and a tert-butyl group.

Examples of the trialkylsilyl group include a trimethylsilyl group and a triethylsilyl group.

Among them, a tert-butyl group is preferable since deprotection is possible even under acidic conditions.

The $R^5$ and $R^6$ each independently represent one of a hydrocarbon group having 1 to 6 carbon atoms and a hydrogen atom, where the $R^5$ and $R^6$ may together form a cyclic structure.

Examples of the hydrocarbon group having 1 to 6 carbon atoms include a methyl group, an ethyl group, an n-propyl group, and an n-butyl group.

The ring structure formed by the $R^5$ in conjunction with the $R^6$ is not particularly limited and can be appropriately selected according to the purpose. Examples thereof include an aliphatic hydrocarbon ring. Examples of the aliphatic hydrocarbon ring include a cyclopentane ring, a cyclohexane ring, and a cycloheptane ring.

With regard to the step of conversion, examples of the cases in which $R^1$ in the general formula (1) is —$OR^{11}$ and —$NR^{12}R^{13}$ will each be explained separately.

Step of conversion A (when $R^1$ in the general formula (1) is —$OR^{11}$)

The step of conversion A can be carried out by, for example, performing the steps of converting a thioamide compound represented by the following general formula (1-1) into a compound represented by the following general formula (5) (Step (A-I)), the compound represented by the following general formula (5) into a compound represented by the following general formula (6) (Step (A-II)), the compound represented by the following general formula (6) into a compound represented by the following general formula (9) (Step (A-III)), the compound represented by the following general formula (9) into a compound represented by the following general formula (11) (Step (A-IV)), and the compound represented by the following general formula (11) into an acetate derivative represented by the general formula (4) (Step (A-V)) in this order.

In the case that the step of conversion A is performed in accordance with the Steps (A-I) to (A-V), step(s) other than those described above can be added while sequentially performing the Steps (A-I) to (A-V).

Also, any of the Steps (A-I) to (A-V) can be replaced by a step other than these steps.

—Step (A-I)—

The step (A-I) is a step of converting a thioamide compound represented by the following general formula (1-1) into a compound represented by the following general formula (5):

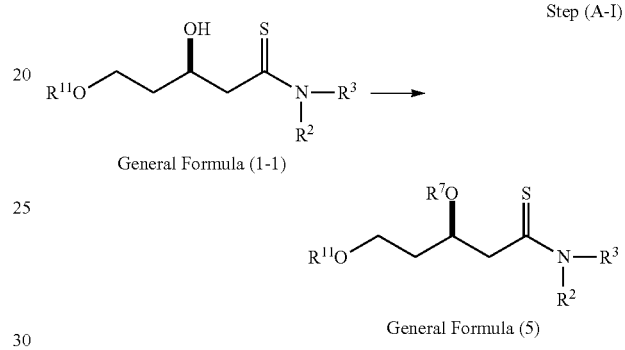

wherein, in the general formula (1-1), $R^2$, $R^3$, and $R^{11}$ are the same as $R^2$, $R^3$, and $R^{11}$, in the general formula (1), respectively. In the general formula (5), $R^2$, $R^3$, and $R^{11}$ are the same as $R^2$, $R^3$, and $R^{11}$ in the general formula (1-1), respectively. The $R^7$ represents a protecting group of a hydroxyl group.

The $R^7$ is not particularly limited as long as it is a protecting group of a hydroxyl group and can be appropriately selected according to the purpose. Examples of the protecting group include those exemplified in the description of the $R^{11}$ in the general formula (1).

A combination of the protecting groups of a hydroxyl group represented by the $R^{11}$ and $R^7$ is not particularly limited and can be appropriately selected according to the purpose, and it is preferable that the group represented by the $R^7$ is more easily removed than the group represented by the $R^{11}$. As such a combination, it is preferable that the $R^{11}$ is a benzyl group and the $R^7$ is a tert-butyldimethylsilyl (TBS) group since the $R^7$ can be selectively removed.

The step (A-I) is not particularly limited as long as the hydrogen atom of the hydroxyl group in the general formula (1-1) can be converted into the $R^7$ group, and can be appropriately selected according to the purpose. For example, this step can be performed in accordance with a publicly known method for protecting a hydroxyl group.

In the step (A-I), when the hydrogen atom of the hydroxyl group in the general formula (1-1) is replaced by a tert-butyldimethylsilyl (TBS) group, it is preferable to carry out the reaction in the presence of a base. The base is not particularly limited and can be appropriately selected according to the purpose. The base is preferably one with low nucleophilicity, more preferably 2,6-lutidine.

—Step (A-II)—

The step (A-II) is a step of converting the compound represented by the general formula (5) into a compound represented by the following general formula (6):

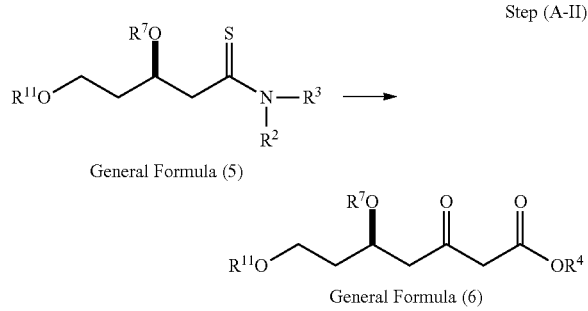

Step (A-II)

General Formula (5)

General Formula (6)

wherein, in the general formula (6), $R^7$ and $R^{11}$ are the same as $R^7$ and $R^{11}$ in the general formula (5), respectively. In the general formula (6), $R^4$ is the same as $R^4$ in the general formula (4).

The Step (A-II) is not particularly limited as long as thioamide can be converted into β keto ester, and can be appropriately selected according to the purpose. For example, this step can be carried out by using an addition reaction of corresponding lithium enolate after S methylation. Also, the Step (A-II) can be carried out with reference to Yuichiro Mutoh, Toshiaki Murai, Organic Letters 2003, Vol. 5, No. 8, pp. 1361 to 1364.

—Step (A-III)—

The Step (A-III) is not particularly limited as long as it is a step of converting a compound represented by the general formula (6) into a compound represented by the following general formula (9), and can be appropriately selected according to the purpose. For example, a method in which diastereoselective reduction is carried out after removing the $R^7$, and then a protecting group is introduced into syn-1,3-diol to form a 1,3-dioxane ring may be performed:

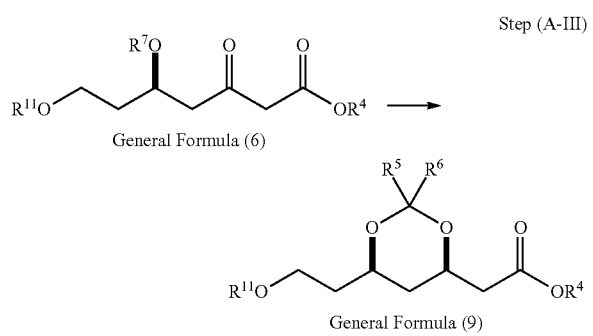

Step (A-III)

General Formula (6)

General Formula (9)

wherein, in the general formula (9), $R^4$ and $R^{11}$ are the same as $R^4$ and $R^{11}$ in the general formula (6), respectively. In the general formula (9), $R^5$ and $R^6$ are the same as $R^5$ and $R^6$ in the general formula (4), respectively.

As the method in which diastereoselective reduction is carried out after removing the $R^7$, and then a protecting group is introduced into syn-1,3-diol to form a 1,3-dioxane ring, for example, a method including performing the steps of converting a compound represented by the general formula (6) into a compound represented by the following general formula (7) (Step (A-III-1)), the compound represented by the following general formula (7) into a compound represented by the following general formula (8) (Step (A-III-2)), and the compound represented by the following general formula (8) into a compound represented by the general formula (9) (Step (A-III-3)) in this order may be performed:

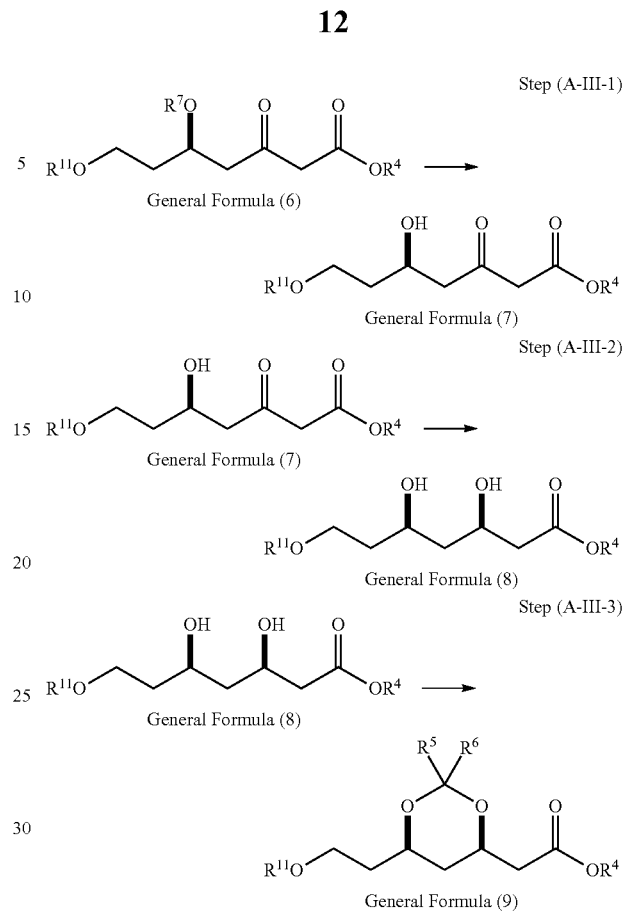

wherein, in the general formulae (7) and (8), $R^4$ and $R^{11}$ are the same as $R^4$ and $R^{11}$ in the general formula (6), respectively.

The Step (A-III-1) is not particularly limited as long as it is a step of replacing the $R^7$ in the general formula (6) by a hydrogen atom, i.e., removing the $R^7$, which is a protecting group of the hydroxyl group, and can be appropriately selected according to the purpose. For example, when the $R^7$ is a trialkylsilyl group (such as a tert-butyldimethylsilyl (TBS) group), a method of deprotection may be performed under acidic conditions or using a fluoride ion. When deprotection is performed using the fluoride ion, for example, tetrabutylammonium fluoride (TBAF), hydrofluoric acid (HF), and cesium fluoride (CsF) can be used.

The Step (A-III-2) is not particularly limited as long as it is a step capable of reducing the carbonyl group in the general formula (7) to a hydroxyl group, and can be appropriately selected according to the purpose. For example, a step using a reducing agent such as $LiAlH_4$ and $NaBH_4$ may be performed. When the $NaBH_4$ is used, reduction is normally performed in the presence of alcohol such as methanol and ethanol. It should be noted that in the Step (A-III-2), syn selectivity can be expressed by controlling the conformation. A method for controlling the conformation is not particularly limited and can be appropriately selected according to the purpose, and for example, the conformation is controlled by forming a chelate between alcohol such as triethyl borane and diethyl methoxy borane and the ketone moiety.

The Step (A-III-3) is not particularly limited as long as it is a step of converting optically active syn-1,3-diol in the general formula (8) into the 1,3-dioxane ring in the general formula (9), and can be appropriately selected according to the purpose. For example, a method using 2,2-dimethoxypropane, 2-methoxy-2-propene, acetone, 3,3-dimethoxy pentane, cyclohexanone, cyclopentanone, and the like may be performed.

In the Step (A-III), it is also possible to perform the Steps (A-III-1) and (A-III-2) without purification, and then perform purification in the Step (A-III-3) to obtain a compound represented by the general formula (9).

—Step (A-IV)—

The Step (A-IV) is not particularly limited as long as it is a step of converting a compound represented by the general formula (9) into a compound represented by the following general formula (11), and can be appropriately selected according to the purpose:

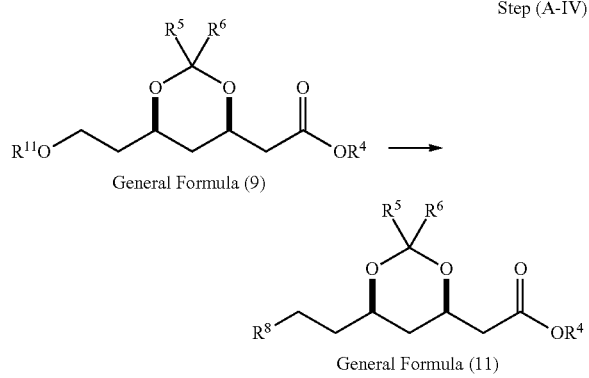

Step (A-IV)

General Formula (9)

General Formula (11)

wherein, in the general formula (11), $R^4$, $R^5$, and $R^6$ are the same as $R^4$, $R^5$, and $R^6$ in the general formula (9), respectively. $R^8$ represents a group that can be converted into an azido group.

The $R^8$ is not particularly limited as long as it is a group that can be converted into an azido group, and can be appropriately selected according to the purpose. Examples thereof include —$OR^{10}$ ($R^{10}$ represents a Ts group (tosyl group), a Ms group (mesyl group), a Tf group (trifluoromethanesulfonyl group), and the like) and an iodine atom.

As the Step (A-IV), for example, a step including converting a compound represented by the general formula (9) into a compound represented by the following general formula (10) (Step (A-IV-1)), and then converting the compound represented by the following general formula (10) into a compound represented by the general formula (11) (Step (A-IV-2)) may be performed:

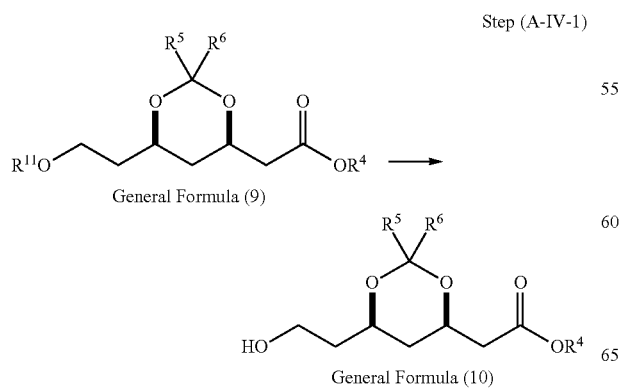

Step (A-IV-1)

General Formula (9)

General Formula (10)

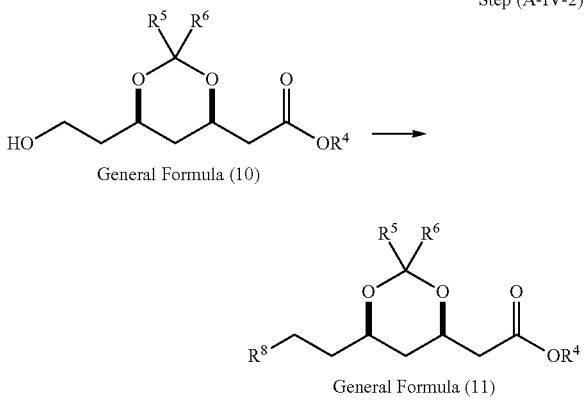

Step (A-IV-2)

General Formula (10)

General Formula (11)

wherein, in the general formula (10), $R^4$, $R^5$, and $R^6$ are the same as $R^4$, $R^5$, and $R^6$ in the general formula (9), respectively.

The Step (A-IV-1) is not particularly limited as long as it is a step of replacing the $R^{11}$ in the general formula (9) by a hydrogen atom, i.e., removing $R^{11}$, which is a protecting group of the hydroxyl group, and can be appropriately selected according to the purpose. This step can be performed by a conventional publicly known method for deprotecting a hydroxyl group. When the $R^{11}$ is a benzyl group, as the Step (A-IV-1), for example, a method for removing the benzyl group by using palladium-carbon (Pd/C) such as palladium hydroxide/carbon (such as Pearlman catalyst) may be performed.

The Step (A-IV-2) is not particularly limited as long as it is a step of replacing the hydroxyl group in the general formula (10) by a group that can be converted into an azido group (for example, —$OR^{10}$ ($R^{10}$ represents a tosyl group)), and can be appropriately selected according to the purpose. For example, a method for tosylating a hydroxyl group using p-toluenesulfonyl chloride may be performed.

In the Step (A-IV), it is also possible to perform the Step (A-IV-1) without purification, and then perform purification in the Step (A-IV-2) to obtain a compound represented by the general formula (11).

—Step (A-V)—

The Step (A-V) is not particularly limited as long as it is a step of converting a compound represented by the general formula (11) into an acetate derivative represented by the following general formula (4), and can be appropriately selected according to the purpose.

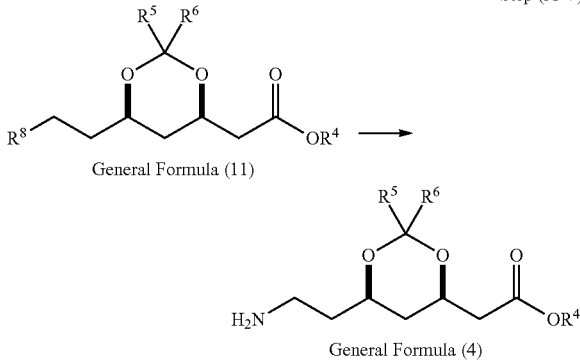

Step (A-V)

General Formula (11)

General Formula (4)

As the Step (A-V), for example, a step including converting a compound represented by the general formula (11) into a compound represented by the following general formula (12) (Step (A-V-1)), and then converting the compound represented by the following general formula (12) into an acetate derivative represented by the general formula (4) (Step (A-V-2)) may be performed:

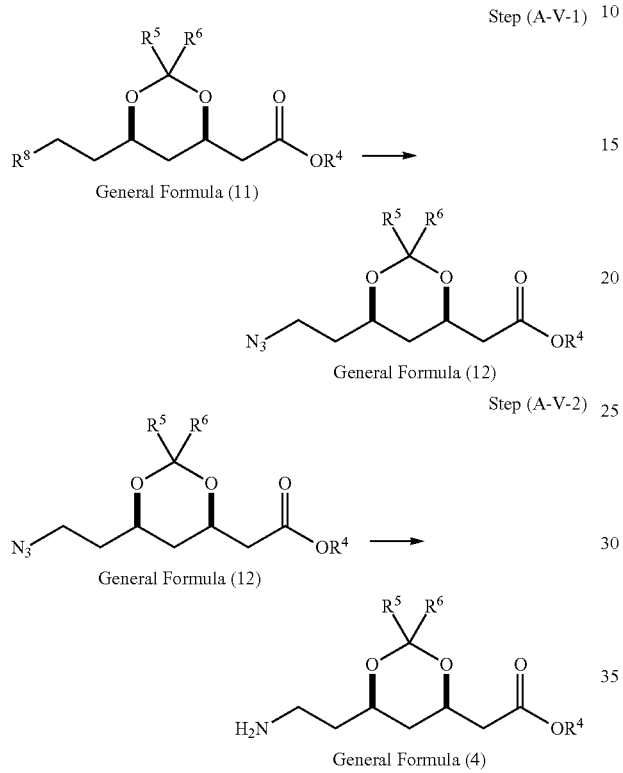

wherein, in the general formula (12), $R^4$, $R^5$, and $R^6$ are the same as $R^4$, $R^5$, and $R^6$ in the general formula (11), respectively.

The Step (A-V-1) is not particularly limited as long as it is a step of replacing $R^8$ (a group that can be converted into an azido group) in the general formula (11) into an azido group ($N_3$—), and can be appropriately selected according to the purpose. For example, when —$OR^{10}$ ($R^{10}$ represents a tosyl group) is replaced by an azido group, a method for producing an azido group, in which sodium azide is reacted as a nucleophilic reagent to carry out a nucleophilic substitution reaction to remove a tosylate anion (TsO⁻), may be performed.

The Step (A-V-2) is not particularly limited as long as it is a step of replacing the azido group ($N_3$—) in the general formula (12) by a primary amino group, and can be appropriately selected according to the purpose. For example, a method using the Staudinger reduction with triphenylphosphine may be performed.

In the Step (A-V), it is also possible to perform the Step (A-V-1) without purification, and then perform purification in the Step (A-V-2) to obtain an acetate derivative represented by the general formula (4).

—Step of Conversion B (when $R^1$ in the General Formula (1) is —$NR^{12}R^{13}$)—

The step of conversion B can be carried out by, for example, performing the steps of converting a thioamide compound represented by the following general formula (1-2) into a compound represented by the following general formula (13) (Step (B-I)), the compound represented by the following general formula (13) into a compound represented by the following general formula (14) (Step (B-II)), the compound represented by the following general formula (14) into a compound represented by the following general formula (17) (Step (B-III)), and the compound represented by the following general formula (17) into an acetate derivative represented by the general formula (4) (Step (B-IV)) in this order.

In the case that the step of conversion B is performed in accordance with the Steps (B-I) to (B-IV), step(s) other than those described above can be added while sequentially performing the Steps (B-I) to (B-IV).

Also, any of the Steps (B-I) to (B-IV) may be replaced by a step other than these steps.

—Step (B-I)—

The step (B-I) is a step of converting a thioamide compound represented by the following general formula (1-2) into a compound represented by the following general formula (13):

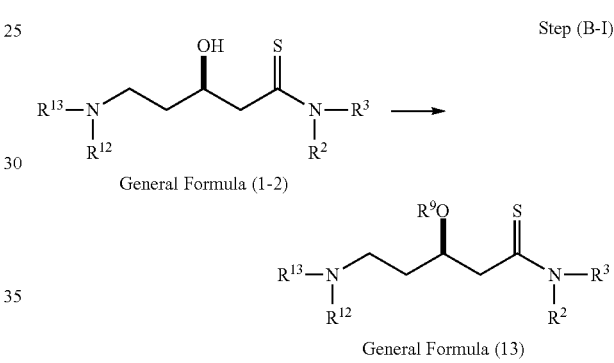

wherein, in the general formula (1-2), $R^2$, $R^3$, $R^{12}$ and $R^{13}$ are the same as $R^2$, $R^3$, $R^{12}$, and $R^{13}$ in the general formula (1), respectively, and in the general formula (13), $R^2$, $R^3$, $R^{12}$, and $R^{13}$ are the same as $R^2$, $R^3$, $R^{12}$, and $R^{13}$ in the general formula (1-2), respectively. The $R^9$ represents a protecting group of a hydroxyl group.

The $R^9$ is not particularly limited as long as it is a protecting group of a hydroxyl group, and can be appropriately selected according to the purpose. Examples of the protecting group include those exemplified in the description of the $R^{11}$ in the general formula (1).

The Step (B-I) is not particularly limited as long as it is capable of converting the hydrogen atom of the hydroxyl group in the general formula (1-2) into the $R^9$ group, and can be appropriately selected according to the purpose. For example, this step can be performed in accordance with a publicly known method for protecting a hydroxyl group.

In the step (B-I), when the hydrogen atom of the hydroxyl group in the general formula (1-2) is replaced by a tert-butyldimethylsilyl (TBS) group, it is preferable to carry out the reaction in the presence of a base. The base is not particularly limited and can be appropriately selected according to the purpose. The base is preferably one with low nucleophilicity, more preferably 2,6-lutidine.

—Step (B-II)—

The step (B-II) is a step of converting a compound represented by the following general formula (13) into a compound represented by the following general formula (14):

Step (B-II)

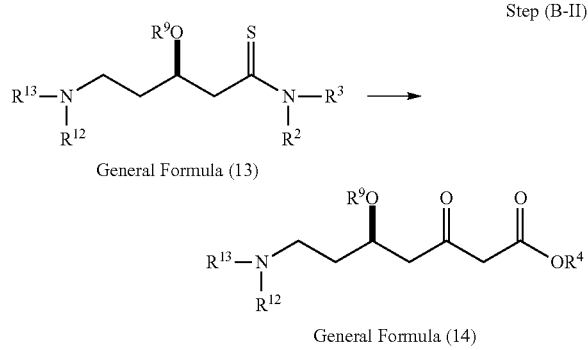

General Formula (13)

General Formula (14)

wherein, in the general formula (14), $R^9$, $R^{12}$, and $R^{13}$ are the same as $R^9$, $R^{12}$, and $R^{13}$ in the general formula (13), respectively. In the general formula (14), $R^4$ is the same as $R^4$ in the general formula (4).

The Step (B-II) is not particularly limited as long as thioamide can be converted into β keto ester, and can be appropriately selected according to the purpose. For example, this step can be carried out by using an addition reaction of corresponding lithium enolate after S methylation. Also, the Step (B-II) can be carried out with reference to Yuichiro Mutoh, Toshiaki Murai, Organic Letters 2003, Vol. 5, No. 8, pp. 1361 to 1364.

—Step (B-III)—

The Step (B-III) is not particularly limited as long as it is a step of converting a compound represented by the general formula (14) into a compound represented by the following general formula (17), and can be appropriately selected according to the purpose. For example, a method in which diastereoselective reduction is carried out after removing the $R^9$, and then a protecting group is introduced into syn-1,3-diol to form a 1,3-dioxane ring may be performed:

Step (B-III)

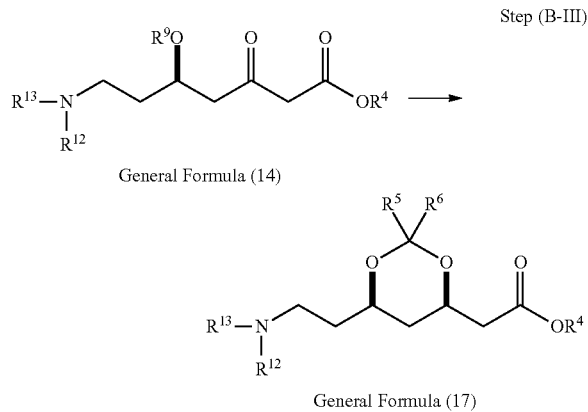

General Formula (14)

General Formula (17)

wherein, in the general formula (17), $R^4$, $R^{12}$, and $R^{13}$ are the same as $R^4$, $R^{12}$, and $R^{13}$ in the general formula (6), respectively. In the general formula (17), $R^5$ and $R^6$ are the same as $R^5$ and $R^6$ in the general formula (4), respectively.

As the method in which diastereoselective reduction is carried out after removing the $R^9$, and then a protecting group is introduced into syn-1,3-diol to form a 1,3-dioxane ring, for example, a method including performing the steps of converting a compound represented by the general formula (14) into a compound represented by the following general formula (15) (Step (B-III-1)), the compound represented by the following general formula (15) into a compound represented by the following general formula (16) (Step (B-III-2)), and the compound represented by the following general formula (16) into a compound represented by the following general formula (17) (Step (B-III-3)) in this order may be performed:

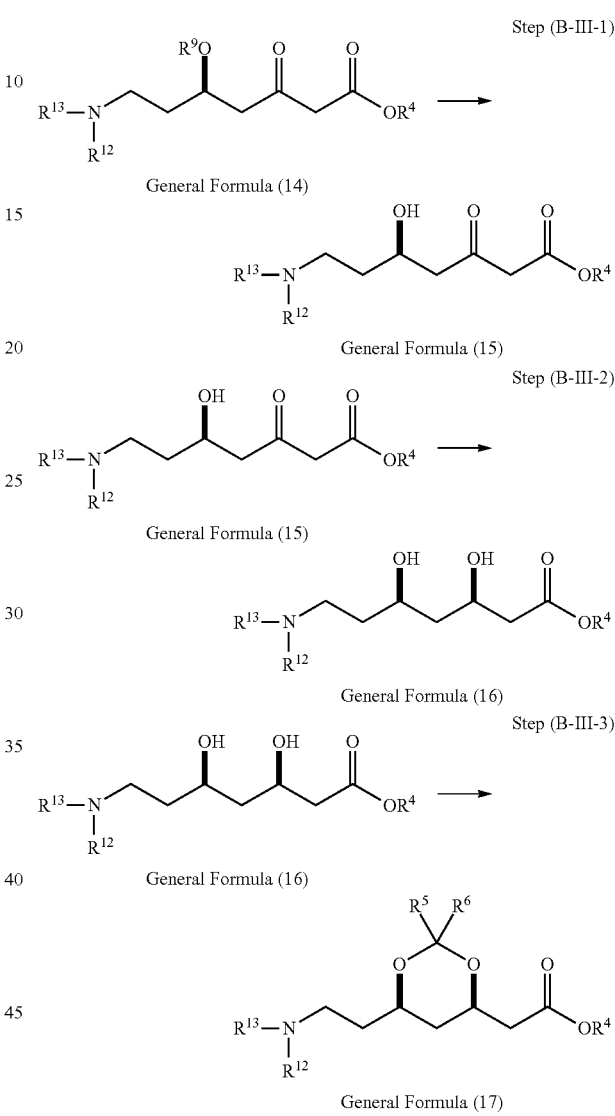

wherein, in the general formulae (15) and (16), $R^4$, $R^{12}$, and $R^{13}$ are the same as $R^4$, $R^{12}$, and $R^{13}$ in the general formula (14), respectively.

The Step (B-III-1) is not particularly limited as long as it is a step of replacing the $R^9$ in the general formula (14) by a hydrogen atom, i.e., removing the $R^9$, which is a protecting group of a hydroxyl group, and can be appropriately selected according to the purpose. For example, when the $R^9$ is a trialkylsilyl group (such as a tert-butyldimethylsilyl (TBS) group), a method of deprotection may be performed under acidic conditions or using a fluoride ion. When deprotection is performed using the fluoride ion, for example, tetrabutylammonium fluoride (TBAF), hydrofluoric acid (HF), and cesium fluoride (CsF) can be used.

The Step (B-III-2) is not particularly limited as long as it is a step capable of reducing the carbonyl group in the general formula (15) to a hydroxyl group, and can be appropriately selected according to the purpose. For example, a step using a reducing agent such as LiAlH$_4$ and NaBH$_4$ may be performed. When the NaBH$_4$ is used, reduction is normally performed in the presence of alcohol such as methanol and ethanol. It should be noted that in the Step (B-III-2) syn selectivity can be expressed by controlling the conformation. A method for controlling the conformation is not particularly limited and can be appropriately selected according to the purpose, and for example, the conformation is controlled by forming a chelate between alcohol such as triethyl borane and diethyl methoxy borane and the ketone moiety.

The Step (B-III-3) is not particularly limited as long as it is a step of converting optically active syn-1,3-diol in the general formula (16) into the 1,3-dioxane ring in the general formula (17), and can be appropriately selected according to the purpose. For example, a method using 2,2-dimethoxypropane, 2-methoxy-2-propene, acetone, 3,3-dimethoxy pentane, cyclohexanone, cyclopentanone, and the like may be performed.

In the Step (B-III), it is also possible to perform the Steps (B-III-1) and (B-III-2) without purification, and then perform purification in the Step (B-III-3) to obtain a compound represented by the general formula (17).

—Step (B-IV)—

The Step (B-IV) is not particularly limited as long as it is a step of converting a compound represented by the general formula (17) into an acetate derivative represented by the general formula (4), and can be appropriately selected according to the purpose.

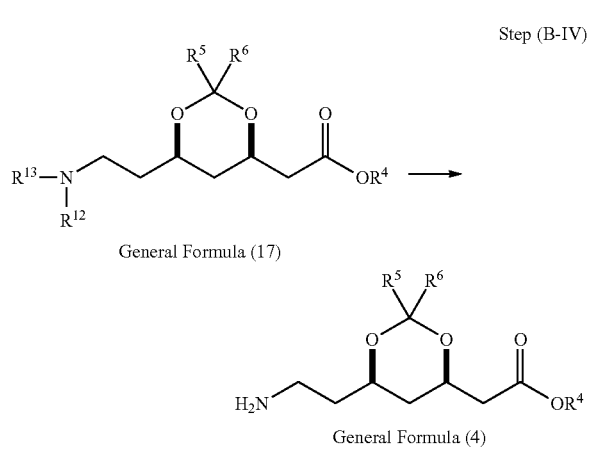

Step (B-IV)

General Formula (17)

General Formula (4)

In the Step (B-IV), a method for converting the NR$^{12}$R$^{13}$ into NH$_2$, i.e., removing the protecting group of the amino group, is not particularly limited, and can be appropriately selected according to the purpose. For example, when the R$^{12}$ and R$^{13}$ together form a phthaloyl group, a method of deprotection utilizing the action of methylamine, hydrazine, and the like may be performed.

The method for producing a [(4R,6R)-6-aminoethyl-1,3-dioxan-4-yl]acetate derivative according to the present invention can produce a [(4R,6R)-6-aminoethyl-1,3-dioxan-4-yl]acetate derivative, which is useful for the production of atorvastatin, efficiently at low cost.

(Method for Producing Atorvastatin)

The aforementioned method for producing atorvastatin at least includes the step of converting a thioamide compound represented by the general formula (1) into an acetate derivative represented by the general formula (4), and if necessary, further includes other steps.

In the present invention, atorvastatin encompasses atorvastatin ((3R,5R)-7-[2-(4-fluorophenyl)-5-isopropyl-3-phenyl-4-phenylcarbamoyl-1H-pyrrol-1-yl]-3,5-dihydroxyheptanoic acid) and pharmaceutically acceptable salts thereof.

Examples of the salt include an alkali metal salt such as a sodium salt and a potassium salt; an alkaline earth metal salt such as a calcium salt and a magnesium salt; an ammonium salt; and an organic base salt such as a trialkylamine salt.

As the atorvastatin, an alkaline earth metal salt of atorvastatin is preferable, and atorvastatin calcium is more preferable.

<Step of Conversion>

Examples of the step of conversion include the step of conversion described in connection with the aforementioned method for producing a [(4R,6R)-6-aminoethyl-1,3-dioxan-4-yl]acetate derivative according to the present invention.

<Other Steps>

Examples of the aforementioned other steps include a step of producing atorvastatin (particularly, atorvastatin calcium) from a [(4R,6R)-6-aminoethyl-1,3-dioxan-4-yl]acetate derivative.

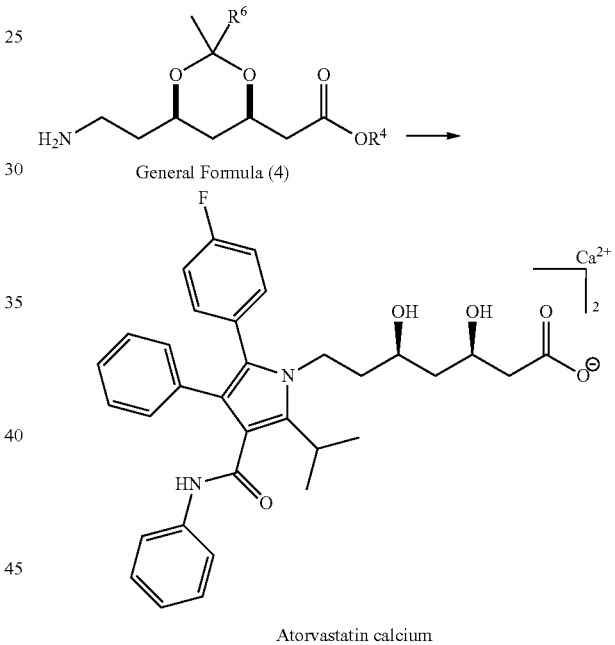

General Formula (4)

Atorvastatin calcium

The step of producing atorvastatin calcium from the [(4R,6R)-6-aminoethyl-1,3-dioxan-4-yl]acetate derivative, i.e., an acetate derivative represented by the general formula (4), is not particularly limited, and can be appropriately selected according to the purpose. For example, the methods described by Kelvin L. Baumann, et al., Tetrahedron Letters, Vol. 33, No. 17, pp. 2283 to 2284, 1992 may be performed.

The method for producing atorvastatin according to the present invention can produce atorvastatin efficiently at low cost.

EXAMPLES

Hereinbelow, the present invention will be specifically described with reference to Examples; however, the present invention is by no means limited to these Examples.

It is to be noted that in the following Examples, "THF" indicates "tetrahydrofuran", "DMF" indicates "N,N-dimeth-

Example 1

Synthesis of a Thioamide Compound A-1, No. 1

Synthesis of a Compound X (N,N-diallylthioacetamide)

Into a 300 mL recovery flask, N,N-diallylacetamide (5.0 g, 36 mmol, 1 equivalent, synthesized according to Stanislaw Krompiec, et al., Journal of Molecular Catalysis A: Chemical 2005, Vil 225, No. 1, pp. 91 to 101), a Lawesson's reagent (7.3 g, 18 mmol, 0.5 equivalent), and dry THF (180 mL) were sequentially added. After heating to reflux for 12 hours, the resulting mixture was brought back to room temperature and 1 N hydrochloric acid (3 mL) was added. The biphasic mixture thus obtained was extracted with ethyl acetate (20 mL), and the resulting organic layer was sequentially washed with saturated sodium bicarbonate water and saturated brine, and then dried over anhydrous sodium sulphate. After filtration and concentration, the residue thus obtained was purified by flash column chromatography (hexane/ethyl acetate=10/1 (volume ratio)) to obtain the following compound X (N,N-diallylthioacetamide) as a light yellow oily matter. Yield 4.8 g (86%).

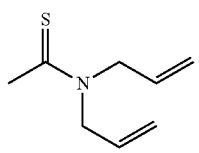

X

Synthesis of 2,2,5,7,8-pentamethylchromanol Lithium Salt

Into a heat-vacuum dried 5 mL recovery flask, 2,2,5,7,8-pentamethylchromanol (88.1 mg, 0.40 mmol) was added, followed by drying under reduced pressure for one hour. The flask was then filled with argon and dried tetrahydrofuran (THF) (2 mL) was added. The flask was cooled to −78° C. in an acetone-dry ice bath, and n-butyllithium (247 µL, 0.40 mmol, 1.62 M hexane solution) was slowly added. The resulting mixture was stirred for one hour at the same temperature to obtain a 0.2 M THF solution of 2,2,5,7,8-pentamethylchromanol lithium salt.

Synthesis of Cu/(S,S)-Ph-BPE

Into a heat-vacuum dried 5 mL recovery flask, [Cu(CH$_3$CN)$_4$]PF$_6$ (manufactured by Strem Chemicals, Inc., 149.0 mg, 0.40 mmol) and (S,S)-Ph-BPE (manufactured by Strem Chemicals, Inc., 202.5 mg, 0.40 mmol) were added in a glove box. Under an argon atmosphere, THF (4 mL) was added to obtain a 0.1 M THF solution of Cu/(S,S)-Ph-BPE (copper-optically active phosphine complex).

Synthesis of a Thioamide Compound A-1

Into a heat-vacuum dried 100 mL recovery flask, N,N-dimethylformamide (DMF) (60 mL), 3-(benzyloxy)propanal (1.0 g, 6.09 mmol, 1 equivalent, synthesized according to Amanda M. Heapy, Margaret A. Brimble, Tetrahedron, Vol. 66, No. 29, pp. 5424 to 5431), N,N-diallylthioacetamide (the compound X, 1.13 g, 7.30 mmol, 1.2 equivalents), and the Cu/(S,S)-Ph-BPE solution prepared as above (3.65 mL, 0.365 mmol, 0.06 equivalent) were added under an argon atmosphere. The recovery flask was transferred to a constant temperature bath of −40° C., and the THF solution of 2,2,5,7,8-pentamethylchromanol lithium salt prepared as above (1.83 mL, 0.365 mmol, 0.06 equivalent) was added, followed by stirring at −40° C. for 36 hours. Subsequently, a saturated aqueous solution of ammonium chloride (30 mL) and 2,2-bipyridine (57 mg, 0.365 mmol, 0.06 equivalent) were added, and the resulting mixture was extracted three times with ethyl acetate (20 mL). The resulting organic layer was sequentially washed with distilled water, saturated sodium bicarbonate water, and saturated brine, and then dried over anhydrous sodium sulphate. After filtration and concentration, the residue thus obtained was purified by flash column chromatography (hexane/ethyl acetate=5/1 to 2/1 (volume ratio)) to obtain the following thioamide compound A-1 as a yellow oily matter. Yield 1.64 g (84%, 92% ee).

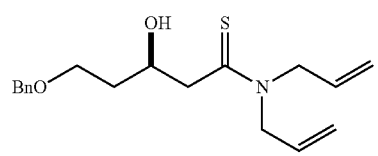

A-1

Chemical Formula: C$_{18}$H$_{25}$NO$_2$S
Exact Mass: 319.1606
Molecular Weight: 319.4616

The IR spectrum, $^1$H NMR spectrum, $^{13}$C NMR spectrum, specific rotation, ESI-MS spectrum, and HRMS spectrum data of the thioamide compound A-1 thus obtained are shown.

IR (neat) ν 3413, 3085, 2919, 2861, 1643, 1496, 1411 cm$^{-1}$ $^1$H NMR (CDCl$_3$) δ 7.34-7.29 (m, 5H), 5.86 (dddd, J=5.7, 5.7, 10.3, 17.2 Hz, 1H), 5.73 (dddd, J=5.0, 5.0, 10.3, 17.2 Hz, 1H), 5.26-5.09 (m, 4H), 4.75 (dd, J=5.7, 14.7 Hz, 1H), 4.54-4.50 (m, 1H), 4.51 (s, 2H), 4.41-4.35 (m, 1H), 4.32-4.25 (m, 1H), 4.10-4.04 (m, 1H), 3.71-3.68 (m, 2H), 2.84 (dd, J=2.8, 15.4 Hz, 1H), 2.76 (dd, J=8.7, 15.4 Hz, 1H), 1.91-1.79 (m, 2H)

$^{13}$CNMR (CDCl$_3$) δ 202.5, 138.1, 130.5, 130.5, 130.5, 128.3, 127.6, 127.5, 118.4, 117.7, 73.1, 69.0, 67.9, 55.5, 52.8, 48.3, 36.3

[α]$_D^{22}$ −33.9 (c0.33, CHCl$_3$, 92% ee sample)

ESI-MS m/z 342.2 [M+Na]$^+$

HRMS (ESI) Anal. calcd. for C$_{18}$H$_{25}$NNaO$_2$S m/z 342.1498 [M+Na]$^+$, found; 342.1500.

Example 2

Synthesis of a Thioamide Compound A-1, No. 2

A thioamide compound A-1 was synthesized using a different kind of catalyst. Specifically, synthesis was carried out as follows.

Into a heat-vacuum dried 20 mL recovery flask, [Cu(CH$_3$CN)$_4$]PF$_6$ (molecular weight, 372.72) (6.7 mg, 0.018 mmol, 0.09 equivalent) and (S)-BINAP (Manufactured by Strem Chemicals, Inc., molecular weight, 622.67, 11.2 mg, 0.018 mmol, 0.09 equivalent) were added in a glove box. Under an argon atmosphere, THF (180 µL) was added, followed by stirring for five minutes. Subsequently, DMF (2 mL), 3-(benzyloxy)propanal (32.8 μL, 0.20 mmol, 1 equivalent) and N,N-diallylthioacetamide (the compound X, 38.2 μL, 0.24 mmol, 1.2 equivalents) were added. The recovery flask was then transferred to a constant temperature bath of −60° C., and a 0.2 M THF solution of 2,2,5,7,8-pentamethylchromanol lithium salt prepared as above (90 μL, 0.018 mmol, 0.09 equivalent) was added, followed by stirring at −60° C. for 60 hours. Subsequently, a THF/acetic acid mixture (10:1 (volume ratio)) (2 mL) and 2,2-bipyridine (2.8 mg, 0.018 mmol, 0.09 equivalent) were added to terminate the reaction. After adding distilled water (2 mL), the resulting mixture was extracted three times with ethyl acetate (2 mL). The resulting organic layer was sequentially washed with saturated sodium bicarbonate water and saturated brine, and then dried over anhydrous sodium sulphate to obtain a thioamide compound A-1 (NMR yield 25%, −10% ee).

Example 3

Synthesis of a Thioamide Compound A-1, No. 3

A thioamide compound A-1 was synthesized using a different kind of catalyst. Specifically, synthesis was carried out as follows.

Into a heat-vacuum dried 20 mL recovery flask, [Cu(CH$_3$CN)$_4$]PF$_6$ (molecular weight, 372.72) (6.7 mg, 0.018 mmol, 0.09 equivalent) and (R,R)-iPr-DuPhos, (molecular weight, 418.58) (7.5 mg, 0.018 mmol, 0.09 equivalent) were added in a glove box. Under an argon atmosphere, THF (180 μL) was added, followed by stirring for five minutes. Subsequently, DMF mL), 3-(benzyloxy)propanal (32.8 μL, 0.20 mmol, 1 equivalent) and N,N-diallylthioacetamide (the compound X, 38.2 μL, 0.24 mmol, 1.2 equivalents) were added. The recovery flask was then transferred to a constant temperature bath of −60° C., and a 0.2 M THF solution of 2,2,5,7,8-pentamethylchromanol lithium salt prepared as above (90 μL, 0.018 mmol, 0.09 equivalent) was added, followed by stirring at −60° C. for 60 hours. Subsequently, a THF/acetic acid mixture (10/1 (volume ratio)) (2 mL) and 2,2-bipyridine (2.8 mg, 0.018 mmol, 0.09 equivalent) were added to terminate the reaction. After adding distilled water (2 mL), the resulting mixture was extracted three times with ethyl acetate (2 mL). The resulting organic layer was sequentially washed with saturated sodium bicarbonate water and saturated brine, and then dried over anhydrous sodium sulphate to obtain a thioamide compound A-1 (NMR yield 52%, −46% ee).

Example 4

Synthesis of a Thioamide Compound A-2

A thioamide compound A-2 having a different kind of protecting group from the thioamide compound A-1 was synthesized. Specifically, synthesis was carried out as follows.

Into a heat-vacuum dried 20 mL recovery flask, DMF (2 mL), 3-(benzyloxy)propanal (33 μL, 0.20 mmol, 1 equivalent, synthesized according to Amanda M. Heapy, Margaret A. Brimble, Tetrahedron, Vol. 66, No. 29, pp. 5424 to 5431), N,N-dimethylthioacetamide (manufactured by Alfa Aesar, 24.5 g, 0.24 mmol, 1.2 equivalents), and the Cu/(S,S)-Ph-BPE solution prepared as above (120 μL, 0.012 mmol, 0.06 equivalent) was added under an argon atmosphere. The recovery flask was transferred to a constant temperature bath of −40° C., and the THF solution of 2,2,5,7,8-pentamethylchromanol lithium salt prepared as above (60 μL, 0.012 mmol, 0.06 equivalent) was added, followed by stirring at −40° C. for 40 hours. Subsequently, a saturated aqueous solution of ammonium chloride (2 mL) and 2,2-bipyridine (1.8 mg, 0.012 mmol, 0.06 equivalent) were added, and the resulting mixture was extracted three times with ethyl acetate (3 mL). The resulting organic layer was sequentially washed with distilled water, saturated sodium bicarbonate water, and saturated brine, and then dried over anhydrous sodium sulphate. After filtration and concentration, the residue thus obtained was purified by flash column chromatography (hexane/ethyl acetate=5/1 to 1/1 (volume ratio)) to obtain the following thioamide compound A-2 as a yellow oily matter. Yield 12.8 mg (24%, 90% ee).

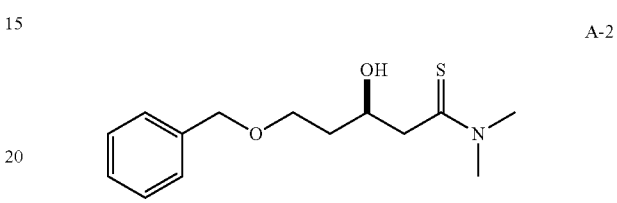

A-2

Chemical Formula: C$_{14}$H$_{21}$NO$_2$S
Exact Mass: 267.1293
Molecular Weight: 267.3870

The IR spectrum, $^1$H NMR spectrum, $^{13}$C NMR spectrum, specific rotation, ESI-MS spectrum, and HRMS spectrum data of the thioamide compound A-2 thus obtained are shown.

IR (neat) ν 3406, 2960, 2871, 1523 cm$^{-1}$ $^1$H NMR (CDCl$_3$) δ 7.36-7.27 (m, 5H), 4.52 (s, 2H), 4.37-4.34 (m, 1H), 3.71-3.69 (m, 2H), 3.46 (s, 3H), 3.28 (s, 3H), 2.79 (dd, J=2.5, 15.8 Hz, 1H), 2.72 (dd, J=8.9, 15.8 Hz, 1H), 1.91-1.84 (m, 2H)

$^{13}$C NMR (CDCl$_3$) δ 202.5, 138.5, 128.3, 127.6, 127.5, 73.1, 69.0, 67.8, 52.9, 44.6, 44.5, 41.9

[α]$_D^{22}$ −34.8 (c0.13, CHCl$_3$, 90% ee)

ESI-MS m/z 280.2 [M+Na]$^+$

HRMS (ESI) Anal. calcd. for C$_{14}$H$_{21}$NNaO$_2$S m/z 290.1185 [M+Na]$^+$, found; 290.1186.

Example 5

Synthesis of a Thioamide Compound A-3

A thioamide compound A-3 having a different kind of protecting group from the thioamide compound A-1 was synthesized. Specifically, synthesis was carried out as follows.

Into a heat-vacuum dried 20 mL recovery flask, DMF (2 mL), 3-(tert-butyldimethylsilyloxy)propanal (37 μL, 0.20 mmol, 1 equivalent, synthesized according to Christian U. Gruenanger, Bernhard Breit, Angewandte Chemie, International Edition, 2010, Vol. 49, No. 5, pp. 967 to 970), N,N-diallylthioacetamide prepared as above (38 μL, 0.24 mmol, 1.2 equivalents), and the Cu/(S,S)-Ph-BPE solution prepared as above (180 μL, 0.018 mmol, 0.09 equivalent) were added under an argon atmosphere. The recovery flask was transferred to a constant temperature bath of −40° C., and the THF solution of 2,2,5,7,8-pentamethylchromanol lithium salt prepared as above (90 μl, 0.018 mmol, 0.09 equivalent) was added, followed by stirring at −40° C. for 40 hours. Subsequently, a saturated aqueous solution of ammonium chloride (2 mL) and 2,2-bipyridine (2.8 mg, 0.018 mmol, 0.06 equivalent) were added, and the resulting mixture was extracted three times with ethyl acetate (3 mL). The resulting organic layer was sequentially washed with distilled water, saturated sodium bicarbonate water, and saturated brine, and then dried over anhydrous sodium sulphate. After filtration and concentration, the residue thus obtained was purified by flash column chromatography (hexane/ethyl acetate=5/1 to 2/1 (volume ratio)) to obtain the following thioamide compound A-3 as a yellow oily matter. Yield 35.7 mg (52%, 45% ee).

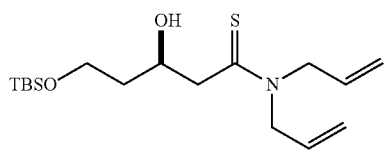

Chemical Formula: $C_{17}H_{33}NO_2SSi$
Exact Mass: 343.2001
Molecular Weight: 343.5999

The IR spectrum, $^1$H NMR spectrum, $^{13}$C NMR spectrum, specific rotation, ESI-MS spectrum, and HRMS spectrum data of the thioamide compound A-3 thus obtained are shown.

IR (neat) v 3421, 2927, 2858, 1643, 1492, 1411, 1250 cm$^{-1}$ $^1$H NMR (CDCl$_3$) δ 5.92 (dddd, J=5.7, 5.7, 10.3, 17.2 Hz, 1H), 5.82 (dddd, J=5.5, 5.5, 10.3, 17.2 Hz, 1H), 5.29-5.15 (m, 4H), 4.77 (dd, J=5.5, 14.9 Hz, 1H), 4.47 (dd, J=6.0, 14.9 Hz, 1H), 4.37-4.32 (m, 2H), 4.14-4.08 (m, 1H), 3.87-3.78 (m, 2H), 2.86-2.81 (m, 2H), 1.81-1.68 (m, 2H), 0.84 (s, 9H), 0.04 (s, 6H)

$^{13}$C NMR (CDCl$_3$) δ 202.7, 130.7, 118.4, 117.8, 69.5, 61.2, 55.7, 53.4, 48.7, 32.2, 25.9, 18.2, −5.5

$[α]_D^{22}$ −17.2 (C0.17, CHCl$_3$, 45% ee)

ESI-MS m/z 366.2 [M+Na]$^+$

HRMS (ESI) Anal. calcd. for $C_{17}H_{33}NNaO_2SSi$ m/z 366.1893 [M+Na]$^+$, found; 366.1892.

Example 6

Synthesis of a Thioamide Compound A-4

A thioamide compound A-4 was synthesized.

Into a heat-vacuum dried 50 mL recovery flask, DMF (13 mL), 3-phthalimidylpropanal (manufactured by Aurora Fine Chemicals, 266.0 mg, 1.13 mmol, 1 equivalent), N,N-diallylthioacetamide (244 μL, 1.35 mmol, 1.2 equivalents), and the Cu/(S,S)-Ph-BPE solution prepared as above (100 μL, 0.10 mmol, 0.09 equivalent) were added under an argon atmosphere. The recovery flask was transferred to a constant temperature bath of −40° C., and the THF solution of 2,2,5,7,8-pentamethylchromanol lithium salt prepared as above (50 μL, 0.10 mmol, 0.09 equivalent) was added, followed by stirring at −40° C. for 24 hours. Subsequently, a saturated aqueous solution of ammonium chloride (5 mL) and 2,2-bipyridine (15.6 mg, 0.10 mmol, 0.09 equivalent) were added, and the resulting mixture was extracted three times with ethyl acetate (5 mL). The resulting organic layer was sequentially washed with distilled water, saturated sodium bicarbonate water, and saturated brine, and then dried over anhydrous sodium sulphate. After filtration and concentration, the residue thus obtained was purified by flash column chromatography (hexane/ethyl acetate=7/1 to 2/1 (volume ratio)) to obtain the following thioamide compound A-4 as a yellow oily matter. Yield 251.1 mg (62%, 75% ee).

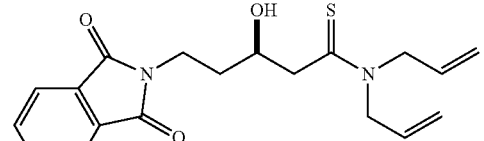

Chemical Formula: $C_{19}H_{22}N_2O_3S$
Exact Mass: 358.1351
Molecular Weight: 358.4546

The IR spectrum, $^1$H NMR spectrum, $^{13}$C NMR spectrum, specific rotation, ESI-MS spectrum, and HRMS spectrum data of the thioamide compound A-4 thus obtained are shown.

IR (neat) v 3463, 3086, 2923, 2865, 1770, 1712, 1612, 1492, 1396 cm$^{-1}$ $^1$H NMR (CDCl$_3$) δ 7.85-7.83 (m, 2H), 7.72-7.71 (m, 2H), 5.86 (dddd, J=6.4, 6.4, 10.7, 17.2 Hz, 1H), 5.78 (dddd, J=4.6, 4.6, 10.7, 17.2 Hz, 1H), 5.30-5.12 (m, 4H), 4.78 (dd, J=4.8, 14.9 Hz, 1H), 4.47 (dd, J=5.7, 14.9 Hz, 1H), 4.36-4.30 (m, 1H), 4.27-4.08 (m, 3H), 3.91-3.84 (m, 2H), 2.78-2.76 (m, 2H), 1.90-1.85 (m, 2H)

$^{13}$C NMR (CDCl$_3$) δ 202.1, 168.5, 133.9, 132.0, 130.6, 130.5, 123.2, 118.5, 118.0, 68.0, 55.7, 53.0, 47.8, 35.2, 34.7

$[α]_D^{22}$ −11.4 (c0.55, CHCl$_3$, 75% ee sample)

ESI-MS m/z 381.4 [M+Na]$^+$

HRMS (ESI) Anal. calcd. for $C_{19}H_{22}N_2NaO_3S$ m/z 381.1243 [M+Na]$^+$, found; 381.1243.

Example 7

Synthesis of Tert-Butyl [(4R,6R)-6-aminoethyl-2,2-dimethyl-1,3-dioxan-4-yl]acetate, No. 1

Synthesis of a Compound B

Into a heat-vacuum dried 100 mL recovery flask, the thioamide compound A-1 synthesized in Example 1 (800 mg, 2.5 mmol, 1 equivalent) and methylene chloride (30 mL) were added under an argon atmosphere, and the resulting mixture was cooled to 0° C. in an ice bath. Subsequently, 2,6-lutidine (575 μL, 5.0 mmol, 2 equivalents) and tert-butyldimethylsilyl (TBS) triflate (860 μL, 3.75 mmol, 1.5 equivalents) were added, followed by stirring at room temperature for three hours. Subsequently, a saturated aqueous solution of ammonium chloride (20 mL) was added to terminate the reaction, and the resulting mixture was extracted three times with methylene chloride (10 mL). The resulting organic layer was washed with saturated brine, and then dried over anhydrous sodium sulphate. After filtration and concentration, a compound B was obtained as a light yellow oily matter. Yield 1.04 g (96%).

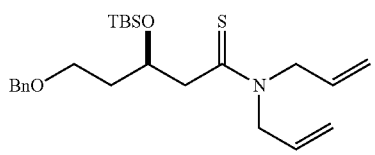

Chemical Formula: C$_{24}$H$_{39}$NO$_2$SSi
Exact Mass: 433.2471
Molecular Weight: 433.7225

The IR spectrum, $^1$H NMR spectrum, $^{13}$C NMR spectrum, specific rotation, ESI-MS spectrum, and HRMS spectrum data of the compound B thus obtained are shown.

IR (neat) ν 2954, 2858, 1643, 1493, 1257, 1115 cm$^{-1}$ $^1$H NMR (CDCl$_3$) δ 7.33-7.29 (m, 5H), 5.92 (dddd, J=5.8, 5.8, 10.8, 16.7 Hz, 1H), 5.75 (dddd, J=4.8, 4.8, 10.3, 17.2 Hz, 1H), 5.25-5.08 (m, 4H), 4.83 (dd, J=5.7, 14.2 Hz, 1H), 4.61-4.53 (m, 2H), 4.48 (dd, J=3.0, 15.1 Hz, 1H), 4.34 (dd, J=6.9, 14.2 Hz, 1H), 4.00-3.95 (m, 1H), 3.64-3.51 (m, 2H), 3.10 (dd, J=8.2, 13.8 Hz, 1H), 2.83 (dd, J=4.1, 13.8 Hz, 1H), 1.90-1.86 (m, 2H), 0.84 (s, 9H), 0.06 (s, 3H), 0.02 (s, 3H)

$^{13}$C NMR (CDCl$_3$) δ 203.0, 138.6, 131.5, 131.3, 128.3, 127.6, 127.5, 119.3, 117.6, 73.0, 72.1, 66.5, 56.4, 53.1, 50.2, 37.4, 25.9, 25.7, 25.6, 17.9, −4.3, −4.8

$[\alpha]_D^{22}$+6.8 (c1.0, CHCl$_3$)

ESI-MS m/z 456.3 [M+Na]$^+$

HRMS (ESI) Anal. calcd. for C$_{24}$H$_{39}$NNaO$_2$SSi m/z 456.2363 m/z [M+Na]$^+$, found; 456.2358.

Synthesis of a Compound C

Preparation of Acetic Acid Tert-butyl Ester Lithium Enolate

Into a heat-vacuum dried 20 mL recovery flask, acetic acid tert-butyl ester (1.0 mL, 7.46 mmol, 1 equivalent) and lithium hexamethyldisilazide (1.25 g, 7.46 mmol, 1 equivalent) were added under an argon atmosphere, and the resulting mixture was cooled to −78° C. in an acetone-dry ice bath. After dropwise addition of dry THF (7.46 mL) cooled to −78° C., the resulting mixture was stirred for one hour at the same temperature to obtain a 1.0 M THF solution of acetic acid tert-butyl ester lithium enolate.

Synthesis of a Compound C

Into a heat-vacuum dried 100 mL recovery flask, the compound B (920 mg, 2.12 mmol, 1 equivalent) and diethyl ether (23 mL) were added under an argon atmosphere, and the resulting mixture was cooled to 0° C. in an ice bath. Methyl triflate (467 μL, 4.24 mmol, 2 equivalents) was added, and the resulting mixture was stirred at 0° C. for five minutes, and then at room temperature for 4.5 hours. The flask was then cooled to −78° C. in an acetone-dry ice bath, and the acetic acid tert-butyl ester lithium enolate prepared as above (64 μL, 6.40 mmol, 3 equivalents) was slowly added dropwise. After stirring for three hours, methylene chloride (7 mL) and silica gel (5 g) were added, followed by stirring at room temperature for 1.5 hours. The mixture thus obtained was passed through a silica gel short pad column and the filtrate was concentrated to obtain a residue. To this residue, THF (20 mL) and 1 N hydrochloric acid (2 mL) were added, followed by stirring at room temperature for two hours. Subsequently, the resulting mixture was extracted three times with ethyl acetate (20 mL). The resulting organic layer was sequentially washed with distilled water, saturated sodium bicarbonate water, and saturated brine, and then dried over anhydrous sodium sulphate. After filtration and concentration, the residue thus obtained was purified by flash column chromatography (hexane/ethyl acetate=20/1 (volume ratio)) to obtain the following compound C as a colorless oily matter. Yield 662 mg (72%).

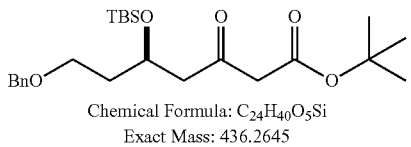

Chemical Formula: C$_{24}$H$_{40}$O$_5$Si
Exact Mass: 436.2645
Molecular Weight: 436.6569

The IR spectrum, $^1$H NMR spectrum, $^{13}$C NMR spectrum, specific rotation, ESI-MS spectrum, and HRMS spectrum data of the compound C thus obtained are shown.

IR (neat) ν 2954, 2931, 2858, 1739, 1716, 1647, 1458, 1369, 1254, 1146, 1115 cm$^{-1}$ $^1$H NMR (CDCl$_3$);

keto form; δ 7.36-7.28 (m, 5H), 4.50 (s, 2H), 4.50-4.43 (m, 1H), 3.56-3.48 (m, 2H), 3.34 (s, 2H), 2.69 (d, J=6.4 Hz, 2H), 1.81-1.77 (m, 2H), 1.45 (s, 9H), 0.85 (s, 9H), 0.05 (s, 3H), 0.03 (s, 3H);

enol form; δ 12.15 (brs, 1H), 7.36-7.28 (m, 5H), 4.90 (s, 1H), 4.33 (s, 2H), 4.35-4.31 (m, 1H), 3.56-3.48 (m, 2H), 2.29 (d, J=6.6 Hz, 2H), 1.77-1.73 (m, 2H), 1.47 (s, 9H), 0.87 (s, 9H), 0.05 (s, 3H), 0.02 (s, 3H)

$^{13}$C NMR (CDCl$_3$) keto-enol mixture; δ 202.1, 166.3, 138.4, 128.3, 127.6, 127.5, 113.9, 92.8, 81.8, 80.6, 73.0, 73.0, 72.9, 67.2, 66.6, 66.4, 52.0, 50.3, 43.8, 37.3, 37.2, 28.6, 28.3, 28.0, 25.8, 17.9, −4.7, −4.8, −4.9

$[\alpha]_D^{22}$−7.6 (c0.5, CHCl$_3$)

ESI-MS m/z 459.3 [M+Na]$^+$

HRMS (ESI) Anal. calcd. for C$_{24}$H$_{40}$NaO$_5$Si m/z 459.2537 [M+Na]$^+$, found; 459.2534.

Synthesis of Compounds D, E, and F

The compound C (400 mg, 0.916 mmol, 1 equivalent) and dry THF (2.5 mL) were put in a 30 mL recovery flask under an argon atmosphere and the resulting mixture was cooled to 0° C. in an ice bath. Subsequently, tetrabutylammonium fluoride (1.3 mL, 1.30 mmol, 1.4 equivalents, a 1.0 M THF solution) was slowly added dropwise, and the resulting mixture was stirred at 0° C. for 30 minutes, and then at room temperature for three hours. Then, distilled water (2 mL) was added, and the resulting mixture was extracted three times with ethyl acetate (5 mL). The resulting organic layer was washed with saturated brine and dried over anhydrous sodium sulphate. After filtration and concentration, a crude product of the following compound D was obtained as a light yellow oily matter.

Subsequently, the compound D obtained as above (292 mg, 0.906 mmol, 1 equivalent), dry THF (8.5 mL), and methanol (2.4 mL) were put in a 50 mL recover flask, and the recover flask was then transferred to a constant temperature bath of −80° C. Subsequently, diethylmethoxyborane (1.0 mL, 1.0 mmol, 1.1 equivalents, a 1.0 M THF solution) was added, followed by stirring for 30 minutes. Subsequently, sodium borohydride (37.8 mg, 1.0 mmol, 1.1 equivalents) was added, followed by stirring at −80° C. for 10 hours. After adding acetic acid (2 mL), the resulting mixture was extracted three times with ethyl acetate (10 mL). The resulting organic layer was sequentially washed with saturated sodium bicarbonate water and saturated brine, and then dried over anhydrous sodium sulphate. After filtration and concentration, a crude product of the following compound E was obtained as a light yellow oily matter.

Into a 30 mL recovery flask, the compound E obtained as above (273 mg, 0.84 mmol, 1 equivalent), acetone (2.6 mL), and p-toluenesulfonic acid monohydrate (16.0 mg) were transferred, and dimethoxypropane (205 μL, 1.68 mmol, 2 equivalents) were added, followed by stirring at room temperature for four hours. Subsequently, saturated bicarbonate water was added to bring pH to about 7, and the resulting mixture was extracted three times with ether (5 mL). The resulting organic layer was washed with saturated brine and dried over anhydrous sodium sulphate. After filtration and concentration, the following compound F was obtained as a light yellow oily matter. Yield 294 mg (three-step yield 88%).

(15.3 mg, 0.125 mmol, 0.3 equivalent), and methylene chloride (2.5 mL) were put in a 20 mL recovery flask, and the resulting mixture was cooled to 0° C. in an ice bath. Triethylamine (17 μL, 1.25 mmol, 3 equivalents) was added, followed by stirring for five minutes, and p-toluenesulfonyl chloride (159.3 mg, 0.834 mmol, 2 equivalents) was added, followed by stirring at room temperature for four hours. Then, methylene chloride (10 mL) and distilled water (10 mL) were added. The resulting organic layer was washed with saturated brine and dried over anhydrous sodium sulphate. After filtration and concentration, the residue thus obtained was purified by flash column chromatography (hexane/ethyl acetate=10/1 to 5/1 (volume ratio)) to obtain a compound H as a colorless oily matter. Yield 165.1 mg (two-step yield 91%).

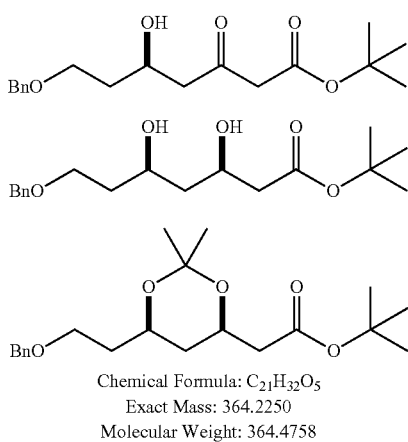

Chemical Formula: $C_{21}H_{32}O_5$
Exact Mass: 364.2250
Molecular Weight: 364.4758

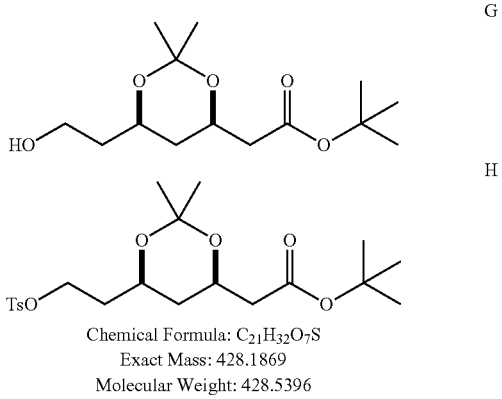

Chemical Formula: $C_{21}H_{32}O_7S$
Exact Mass: 428.1869
Molecular Weight: 428.5396

The IR spectrum, $^1$H NMR spectrum, $^{13}$C NMR spectrum, specific rotation, ESI-MS spectrum, and HRMS spectrum data of the compound F thus obtained are shown.

IR (neat) ν 2981, 2938, 1724, 1454, 1369, 1277, 1153 cm$^{-1}$
$^1$H NMR (CDCl$_3$) δ 7.38-7.27 (m, 5H), 4.50 (dd, J=4.8, 12.1 Hz, 2H), 4.28-4.21 (m, 1H), 4.09-4.02 (m, 1H), 3.61-3.50 (m, 2H), 2.42 (dd, J=7.1, 15.1 Hz, 1H), 2.29 (dd, J=6.2, 15.1 Hz, 1H), 1.81-1.68 (m, 2H), 1.56 (dt, J=2.3, 12.6 Hz, 1H), 1.44 (s, 9H), 1.44 (s, 3H), 1.35 (s, 3H), 1.25-1.15 (m, 1H)
$^{13}$C NMR (CDCl$_3$) δ 170.3, 138.5, 128.4, 127.6, 127.5, 98.7, 80.5, 73.0, 66.3, 66.2, 66.0, 42.8, 36.6, 36.5, 30.1, 28.1, 19.6
$[\alpha]_D^{22}$+21.9 (c0.26, CHCl$_3$)
ESI-MS m/z 387.2 [M+Na]$^+$
HRMS (ESI) Anal. calcd. for $C_{21}H_{32}NaO_5$ m/z 387.2142 [M+Na]$^+$, found; 387.2140.

Synthesis of Synthesized Parts G and H

Into a 20 mL recovery flask, the compound F (153 mg, 0.419 mmol, 1 equivalent), ethyl acetate (1.5 mL), and palladium hydroxide/carbon (25 mg, 20% w/w) were added, and the resulting mixture was stirred at 60° C. for 24 hours under a hydrogen atmosphere at 1 atm. Subsequently, unnecessary substances were filtered off through Celite and the resulting filtrate was concentrated under reduced pressure to obtain the following compound G as a light yellow oily matter.

Subsequently, the compound G obtained as above (120.5 mg, 0.417 mmol, 1 equivalent), 4-dimethylaminopyridine The IR spectrum, $^1$H NMR spectrum, $^{13}$C NMR spectrum, specific rotation, ESI-MS spectrum, and HRMS spectrum data of the compound H thus obtained are shown.

IR (neat) ν 2981, 1728, 1365, 1176 cm$^{-1}$
$^1$H NMR (CDCl$_3$) δ 7.91 (d, J=8.2 Hz, 2H), 7.79 (d, 4H), 7.34 (d, J=8.2 Hz, 2H), 4.26-4.18 (m, 1H), 4.18-4.13 (m, 1H), 4.11-4.06 (m, 1H), 3.99-3.91 (m, 1H), 2.45 (s, 3H), 2.39 (dd, J=7.1, 15.1 Hz, 1H), 2.26 (dd, J=6.2, 15.1 Hz, 1H), 1.89-1.67 (m, 2H), 1.51-1.45 (m, 2H), 1.44 (s, 9H), 1.34 (s, 3H), 1.27 (s, 3H)
$^{13}$C NMR (CDCl$_3$) δ 170.1, 144.7, 133.0, 129.8, 127.9, 98.8, 80.6, 66.7, 66.0, 64.7, 42.6, 36.2, 35.4, 29.9, 28.1, 21.6, 19.5
$[\alpha]_D^{22}$+12.9 (c0.9, CHCl$_3$)
ESI-MS m/z 451.2 [M+Na]$^+$
HRMS (ESI) Anal. calcd. for $C_{21}H_{32}NaO_7S$ m/z 451.1761 [M+Na]$^+$, found; 451.1756.

Synthesis of Compounds I and J

Into a 20 mL recovery flask, the compound H (120.0 mg, 0.277 mmol, 1 equivalent), sodium azide (36.0 mg, 0.555 mmol, 2 equivalents), and N,N-dimethylformamide (1.5 mL) were added, followed by stirring at room temperature for six hours. Subsequently, distilled water (1 mL) was added. The resulting mixture was extracted with ethyl acetate (3 mL), and the resulting organic layer was washed with saturated brine and dried over anhydrous sodium sulphate. The mixture thus obtained was passed through a silica gel short pad column and the filtrate was concentrated to obtain the following compound I. Yield 67.8 mg (82%).

The compound I (52.1 mg, 0.174 mmol, 1 equivalent), THF (1.0 mL), distilled water (0.10 mL), and triphenylphosphine (91.3 mg, 0.348 mmol, 2 equivalents) were put in a 10 mL test tube, and the resulting mixture was stirred at 50° C. for two hours. THF was then distilled away under reduced pressure. To the residue thus obtained, toluene (5 mL) was added, and the resulting mixture was concentrated under reduced pressure. Water contained in the residue was distilled away as an azeotropic mixture. To the residue thus obtained, toluene (5 mL) was added again and the resulting mixture was concentrated under reduced pressure. The residue thus obtained was purified by flash column chromatography (methylene chloride/methanol/triethylamine=95/4/1 (volume ratio)) to obtain a compound J (tert-butyl [(4R,6R)-6-aminoethyl-2,2-dimethyl-1,3-dioxan-4-yl]acetate) as a colorless oily matter. Yield 41.2 mg (87%).

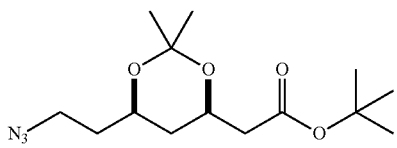

I

Chemical Formula: $C_{14}H_{25}N_3O_4$
Exact Mass: 299.1845
Molecular Weight: 299.3660

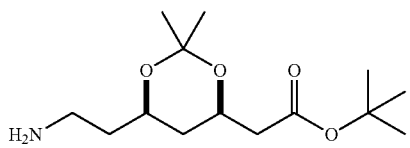

J

Chemical Formula: $C_{14}H_{27}NO_4$
Exact Mass: 273.1940
Molecular Weight: 273.3685

The IR spectrum, $^1$H NMR spectrum, $^{13}$C NMR spectrum, specific rotation, ESI-MS spectrum, and HRMS spectrum data of the compound I thus obtained are shown.

IR (neat) v 2978, 2939, 2877, 2098, 1732 cm$^{-1}$ $^1$H NMR (CDCl$_3$) δ 4.37-4.30 (m, 1H), 4.12-4.06 (m, 1H), 3.48-3.41 (m, 2H), 2.37 (dd, J=5.5, 14.9 Hz, 1H), 2.33 (dd, J=7.6, 14.9 Hz, 1H), 1.80-1.65 (m, 2H), 1.66 (dt, 2.5, 12.6 Hz, 1H), 1.48 (s, 3H), 1.46 (s, 9H), 1.32 (s, 3H), 1.22-1.13 (m, 1H)

$^{13}$C NMR (CDCl$_3$) δ 170.1, 98.8, 80.6, 66.1, 65.8, 47.5, 42.6, 36.4, 35.6, 30.0, 28.1, 19.6

$[α]_D^{22}$+17.9 (c0.21, CHCl$_3$)

ESI-MS m/z 322.2 [M+Na]$^+$

HRMS (ESI) Anal. calcd. for $C_{14}H_{25}N_3NaO_4$ m/z 322.1737 [M+Na]$^+$, found; 322.1737.

The IR spectrum, $^1$H NMR spectrum, $^{13}$C NMR spectrum, specific rotation, ESI-MS spectrum, and HRMS spectrum data of the compound J thus obtained are shown.

IR (neat) v 3374, 2981, 2938, 2873, 1731, 1176 cm$^{-1}$ $^1$H NMR (CDCl$_3$) δ 4.25-4.19 (m, 1H), 3.98-3.92 (m, 1H), 2.80-2.77 (m, 2H), 2.39 (dd, J=6.9, 15.1, 1H), 2.26 (dd, J=6.2, 15.1, 1H), 1.95 (brs, 2H), 1.64-1.50 (m, 3H), 1.42 (s, 9H), 1.42 (s, 3H), 1.33 (5, 3H), 1.30-1.15 (m, 1H)

$^{13}$C NMR (CDCl$_3$) δ 170.2, 98.6, 80.5, 67.4, 66.2, 42.6, 39.5, 38.4, 36.5, 30.1, 28.0, 19.7

$[α]_D^{22}$+11.5 (c0.28, CHCl$_3$)

ESI-MS m/z 274.2 [M+H]$^+$

HRMS (ESI) Anal. calcd. for $C_{14}H_{28}NO_4$ m/z 274.2013 [M+H]$^+$, found; 274.2015.

Example 8

Synthesis of Tert-butyl [(4R,6R)-6-aminoethyl-2,2-dimethyl-1,3-dioxan-4-yl]acetate, No. 2

Synthesis of a Compound K

Into a heat-vacuum dried 30 mL recovery flask, the thioamide compound A-4 synthesized in Example 6 (100.2 mg, 0.28 mmol, 1 equivalent) and methylene chloride (3.5 mL) were added under an argon atmosphere, and the resulting mixture was cooled to 0° C. in an ice bath. Subsequently, 2,6-lutidine (64.0 μL, 0.56 mmol, 2 equivalents) and tert-butyldimethylsilyl (TBS) triflate (96.5 μL, 0.42 mmol, 1.5 equivalents) were added, followed by stirring at room temperature for three hours. Subsequently, a saturated aqueous solution of ammonium chloride (3 mL) was added to terminate the reaction, and the resulting mixture was extracted three times with methylene chloride (5 mL). The resulting organic layer was washed with saturated brine, and then dried over anhydrous sodium sulphate. After filtration and concentration, the following compound K was obtained as a light yellow oily matter. Yield 124.4 mg (94%).

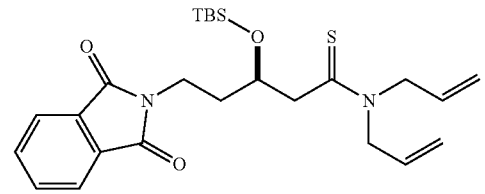

K

Chemical Formula: $C_{25}H_{36}N_2O_3SSi$
Exact Mass: 472.2216
Molecular Weight: 472.7154

The IR spectrum, $^1$H NMR spectrum, $^{13}$C NMR spectrum, specific rotation, ESI-MS spectrum, and HRMS spectrum data of the compound K thus obtained are shown.

IR (neat) v 2954, 2857, 1774, 1712, 1593, 1496, 1400 cm$^{-1}$ $^1$H NMR (CDCl$_3$) δ 7.82-7.80 (m, 2H), 7.71-7.68 (m, 2H), 5.92 (dddd, J=5.7, 5.7, 10.3, 17.2 Hz, 1H), 5.82 (dddd, J=5.5, 5.5, 10.3, 17.2 Hz, 1H), 5.27-5.11 (m, 4H), 4.85 (dd, J=7.2, 14.2 Hz, 1H), 4.63-4.53 (m, 2H), 4.31 (dd, J=7.3, 14.2 Hz, 1H), 4.00 (dd, J=4.6, 17.2 Hz, 1H), 3.82-3.72 (m, 2H), 3.16 (dd, J=8.5, 13.5 Hz, 1H), 2.81 (dd, J=4.1, 13.5 Hz, 1H), 2.03-1.86 (m, 2H), 0.85 (s, 9H), 0.10 (s, 3H), 0.03 (s, 3H)

$^{13}$C NMR (CDCl$_3$) δ 202.5, 168.2, 133.8, 132.2, 131.3, 131.2, 123.1, 119.4, 117.6, 72.2, 56.5, 53.1, 49.1, 35.7, 34.0, 25.8, 17.8, −4.4, −4.7

$[α]_D^{23}$+10.1 (C0.19, CHCl$_3$)

ESI-MS m/z 495.2 [M+Na]$^+$

HRMS (ESI) Anal. calcd. for $C_{25}H_{36}N_2NaO_3SSi$ m/z 495.2108 m/z [M+Na]$^+$, found; 495.2111

Synthesis of Compounds L, M, N, and O

Into a heat-vacuum dried 20 mL test tube, the compound K (83.5 mg, 0.177 mmol, 1 equivalent) and diethyl ether (1.5 mL) were added under an argon atmosphere, and the resulting mixture was cooled to 0° C. in an ice bath. Subsequently, methyl triflate (39 mL, 0.353 mmol, 2 equivalents) was added, and the resulting mixture was stirred at 0° C. for five minutes, and then at room temperature for 4.5 hours. The flask was then cooled to −78° C. in an acetone-dry ice bath, and the acetic acid tert-butyl ester lithium enolate prepared as above (177 µL, 0.177 mmol, 3 equivalents) was slowly added dropwise. After stirring for three hours, methylene chloride (3 mL) and silica gel (2 g) were added, followed by stirring at room temperature for 1.5 hours. The mixture thus obtained was passed through a silica gel short pad column and the filtrate was concentrated to obtain a residue. To this residue, THF (10 mL) and 1 N hydrochloric acid (1 mL) were added, followed by stirring at room temperature for two hours. Subsequently, the resulting mixture was extracted three times with ethyl acetate (5 mL). The resulting organic layer was sequentially washed with distilled water, saturated sodium bicarbonate water, and saturated brine, and then dried over anhydrous sodium sulphate. After filtration and concentration, a crude product of the following compound L was obtained as a light yellow oily matter.

Subsequently, under an argon atmosphere, the compound L (60 mg, 0.126 mmol, 1 equivalent) and dry THF (800 µL) were transferred to a 20 mL test tube, and the resulting mixture was cooled to 0° C. in an ice bath. Subsequently, tetrabutylammonium fluoride (176 mL, 0.176 mmol, 1.4 equivalents, a 1.0 M THF solution) was slowly added dropwise, and the resulting mixture was stirred at 0° C. for 30 minutes, and then at room temperature for three hours. Distilled water (0.5 mL) was added, and the resulting mixture was extracted three times with ethyl acetate (3 mL). The resulting organic layer was washed with saturated brine and dried over anhydrous sodium sulphate. After filtration and concentration, a crude product of the following compound M was obtained as a light yellow oily matter.

Subsequently, the compound M (45 mg, 0.124 mmol, 1 equivalent), dry THF (1.7 mL), and methanol (0.4 mL) were put in a 20 mL recovery flask, and the recovery flask was transferred to a constant temperature bath of −80° C. Subsequently, diethylmethoxyborane (136 µL, 0.136 mmol, 1.1 equivalents, a 1.0 M THF solution) was added, followed by stirring for 30 minutes. Subsequently, sodium borohydride (5.2 mg, 0.136 mmol, 1.1 equivalents) was added, followed by stirring at −80° C. for 10 hours. After adding acetic acid (0.2 mL), the resulting mixture was extracted three times with ethyl acetate (3 mL). The resulting organic layer was sequentially washed with saturated sodium bicarbonate water and saturated brine, and then dried over anhydrous sodium sulphate. After filtration and concentration, a crude product of the following compound N was obtained as a light yellow oily matter.

Subsequently, the compound N thus obtained (43.0 mg, 0.12 mmol, 1 equivalent), acetone (0.5 mL), and p-toluenesulfonic acid monohydrate (2.3 mg, 0.012 mmol, 0.1 equivalent) were transferred to a 20 mL test tube, and dimethoxypropane (29.5 µL, 0.24 mmol, 2 equivalents) was added, followed by stirring at room temperature for four hours. Subsequently, saturated bicarbonate water was added to bring pH to about 7, and the resulting mixture was extracted three times with ether (2 mL). The resulting organic layer was washed with saturated brine and dried over anhydrous sodium sulphate. After filtration and concentration, a compound O was obtained as a light yellow oily matter. Yield 47 mg (four-step yield 66%).

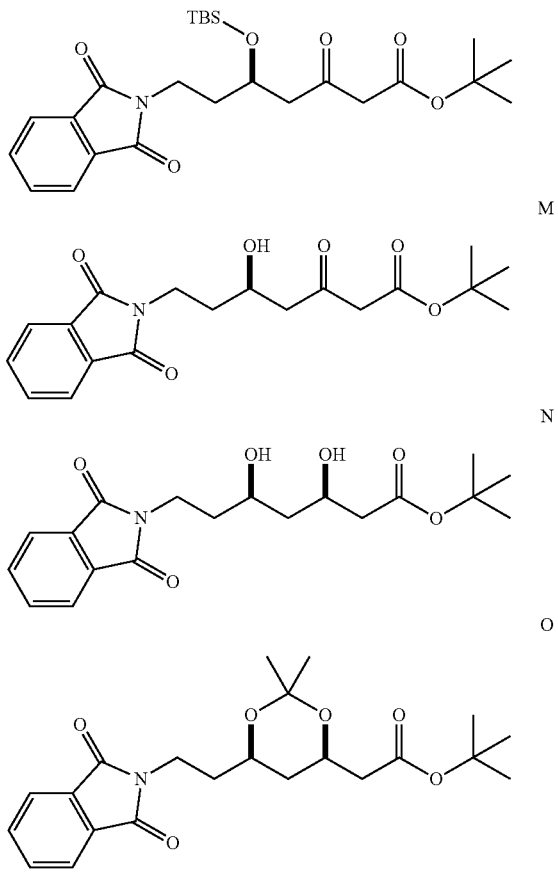

Chemical Formula: $C_{22}H_{29}NO_6$
Exact Mass: 403.1995
Molecular Weight: 403.4688

The IR spectrum, $^1$H NMR spectrum, and $^{13}$C NMR spectrum data of the compound O thus obtained are shown.

IR (neat) ν 2923, 2865, 1770, 1725, 1712, 1612, 1492, 1396 cm$^{-1}$ $^1$H NMR (CDCl$_3$) δ 7.86-7.83 (m, 2H), 7.74-7.71 (m, 2H), 4.35-4.27 (m, 1H), 4.12-4.04 (m, 1H), 3.65-3.55 (m, 2H), 2.44 (dd, J=7.1, 15.1 Hz, 1H), 2.32 (dd, J=6.2, 15.1 Hz, 1H), 1.82-1.69 (m, 2H), 1.57 (dt, J=2.3, 12.6 Hz, 1H), 1.44 (s, 9H), 1.44 (s, 3H), 1.35 (s, 3H), 1.25-1.15 (m, 1H)

$^{13}$C NMR (CDCl$_3$) δ 170.5, 168.6, 133.9, 132.0, 130.6, 80.5, 73.0, 67.9, 66.2, 42.8, 36.7, 36.6, 33.1, 30.1, 28.1, 19.6

Synthesis of a Compound J

The compound O (45 mg, 0.11 mmol, 1 equivalent) was dissolved in ethanol (2.5 mL), and hydrazine monohydrate (70 mL, 2.25 mmol, 20 equivalents) was added, followed by stirring at 60° C. for one hour. After bringing the resulting reaction solution to room temperature, the precipitated solids were filtered off and the filtrate was concentrated under reduced pressure. To the residue, methylene chloride and saturated brine were added, and the resulting aqueous layer was extracted with methylene chloride. The resulting organic layer was dried over anhydrous sodium sulphate. After filtration and concentration, the residue thus obtained was purified by flash column chromatography (methylene chloride/ methanol/triethylamine=95/4/1 (volume ratio)) to obtain a compound J as a colorless oily matter. Yield 25.5 mg (85%).

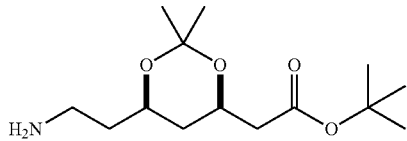

INDUSTRIAL APPLICABILITY

Since the thioamide compound of the present invention enables efficient production of a [(4R,6R)-6-aminoethyl-1,3-dioxan-4-yl]acetate derivative at low cost, the thioamide compound of the present invention can be favorably used for the synthesis of atorvastatin.

What is claimed is:

1. A thioamide compound represented by the following general formula (1):

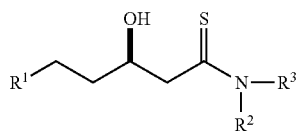

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure.

2. A method for producing a thioamide compound represented by the following general formula (1), the method comprising:

reacting a compound represented by the following general formula (2) with a compound represented by the following general formula (3) to obtain the thioamide compound represented by the following general formula (1):

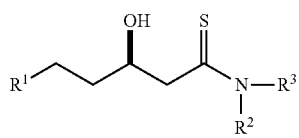

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure,

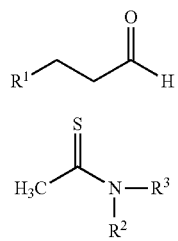

General Formula (2)

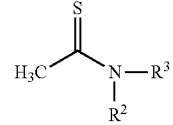

General Formula (3)

wherein, in the general formula (2), $R^1$ represents one of —$OR^{11}$ and —$NR^{12}R^{13}$; the $R^{11}$ represents one of a protecting group of a hydroxyl group and a hydrogen atom; the $R^{12}$ and $R^{13}$ each independently represent one of a hydrogen atom and a protecting group of an amino group, where the $R^{12}$ and $R^{13}$ may together form a protecting group having a cyclic structure; and in the general formula (3), $R^2$ and $R^3$ each independently represent one of a protecting group of an amide group and a hydrogen atom.

3. The method for producing the thioamide compound according to claim 2, wherein the reacting is carried out with a copper complex.

4. The method for producing the thioamide compound according to claim 3, wherein the copper complex is a copper-optically active phosphine complex.

5. A method for producing atorvastatin, comprising:
converting a thioamide compound represented by the following general formula (1) into an acetate derivative represented by the following general formula (4) and converting the acetate derivative represented by the following general formula (4) into atorvastatin:

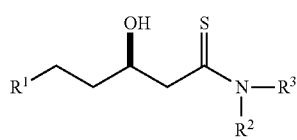

General Formula (1)

wherein, in the general formula (1), $R^1$ represents one of —$OR^{11}$ and —$NR^{12}R^{13}$; $R^2$ and $R^3$ each independently represent one of a protecting group of an amide group and a hydrogen atom; the $R^{11}$ represents one of a protecting group of a hydroxyl group and a hydrogen atom; and the $R^{12}$ and $R^{13}$ each independently represent one of a protecting group of an amino group and a hydrogen atom, where the $R^{12}$ and $R^{13}$ may together form a protecting group having a cyclic structure, and

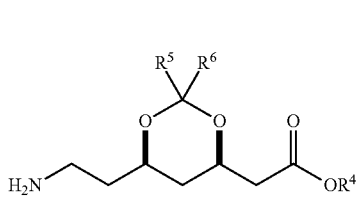

General Formula (4)

wherein, in the general formula (4), $R^4$ represents one of a protecting group of a carboxyl group and a hydrogen atom; and $R^5$ and $R^6$ each independently represent one of a hydrocarbon group having 1 to 6 carbon atoms and a hydrogen atom, where the $R^5$ and $R^6$ may together form a cyclic structure.

* * * * *